United States Patent [19]

Jackman et al.

[11] Patent Number: 4,572,192
[45] Date of Patent: Feb. 25, 1986

[54] SYSTEM FOR PREVENTION OF PAROXYSMAL SUPRAVENTRICULAR TACHYCARDIA

[75] Inventors: Warren M. Jackman, Edmond; Ralph Lazzara, Oklahoma City, both of Okla.

[73] Assignee: Board of Regents for The University of Oklahoma, Norman, Okla.

[21] Appl. No.: 534,367

[22] Filed: Sep. 21, 1983

[51] Int. Cl.$^4$ .............................................. A61N 1/36
[52] U.S. Cl. ............................................. 128/419 PG
[58] Field of Search ................... 128/419 PG, 419 PT

[56] References Cited

U.S. PATENT DOCUMENTS

| | | | |
|---|---|---|---|
| 3,693,626 | 9/1972 | Cole | 128/419 PG |
| 4,052,991 | 10/1977 | Zacouto | 128/419 |
| 4,452,248 | 6/1984 | Keller, Jr. | 128/419 PG |

FOREIGN PATENT DOCUMENTS 81209  6/1983  European Pat. Off. ..... 128/419 PG

*Primary Examiner*—William E. Kamm
*Attorney, Agent, or Firm*—Dunlap, Codding & Peterson

[57] ABSTRACT

A system for aborting the dual pathway tachycardias in a heart comprising the syndrome of paroxysmal supraventricular tachycardia (due generally to atrioventricular nodal reentry or atrioventricular reentry using an anomalous atrioventricular connection for retrograde conduction) by sensing cardiac impulses and, with respect to each sensed cardiac impulse, determining if such sensed cardiac impulse is an inciting cardiac impulse, a cardiac impulse which occurs at a time with respect to the last received cardiac impulse which falls within a predetermined echo zone and which will result in the initiation of a dual pathway tachycardia, and inducing an aborting cardiac impulse in response to a sensed inciting cardiac impulse in the cardiac muscle at a time within the predetermined aborting zone for aborting the initiation of the dual pathway tachycardia. The system also contemplates sensing cardiac impulses and delivering aborting electrical stimuli at a particular position on the cardiac muscle to allow more accurate recognition of inciting cardiac impulses and for more effectively delivering the aborting electrical stimulus, inducing the aborting cardiac impulse in sufficient time to abort the onset of dual pathway tachycardia.

60 Claims, 18 Drawing Figures

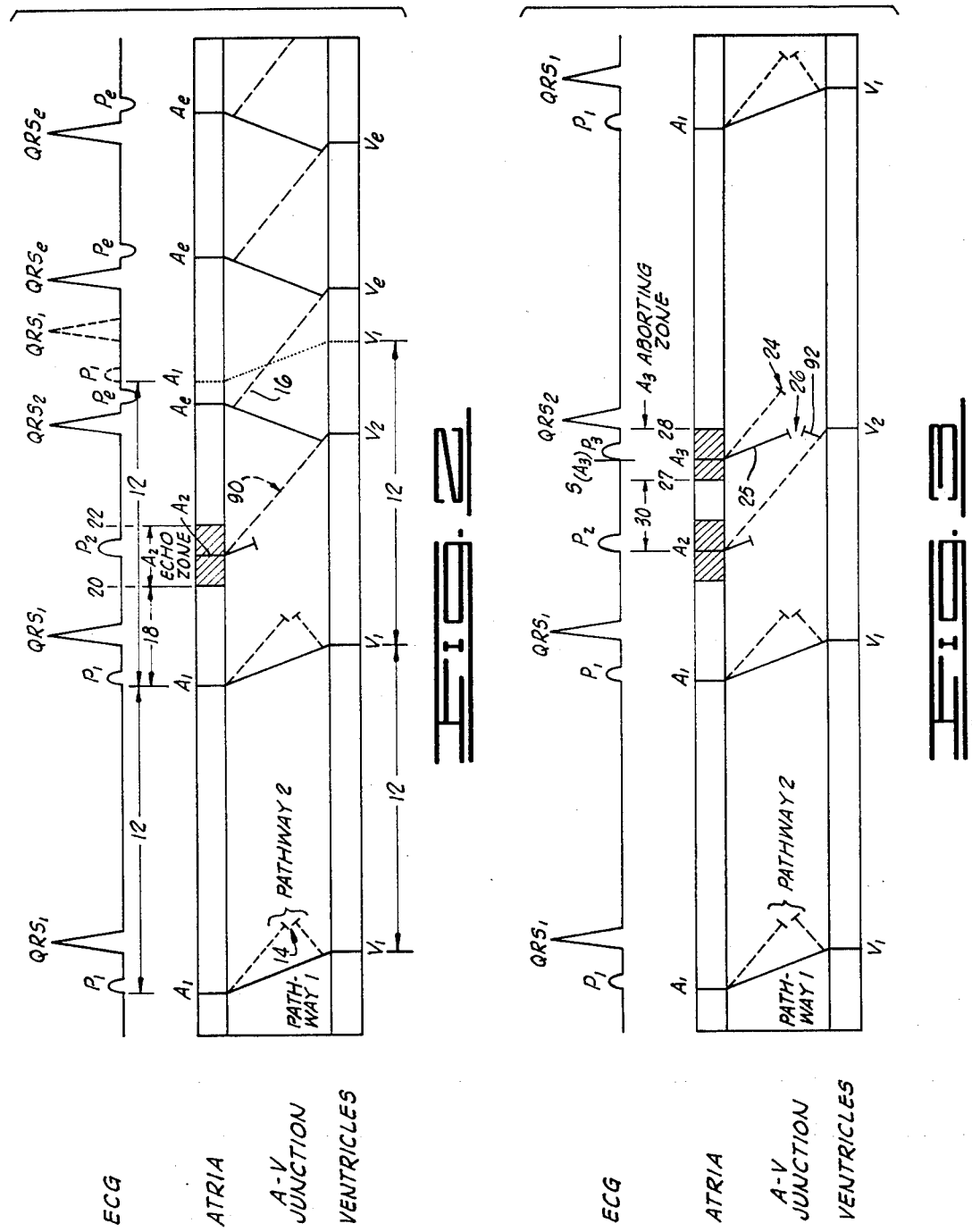

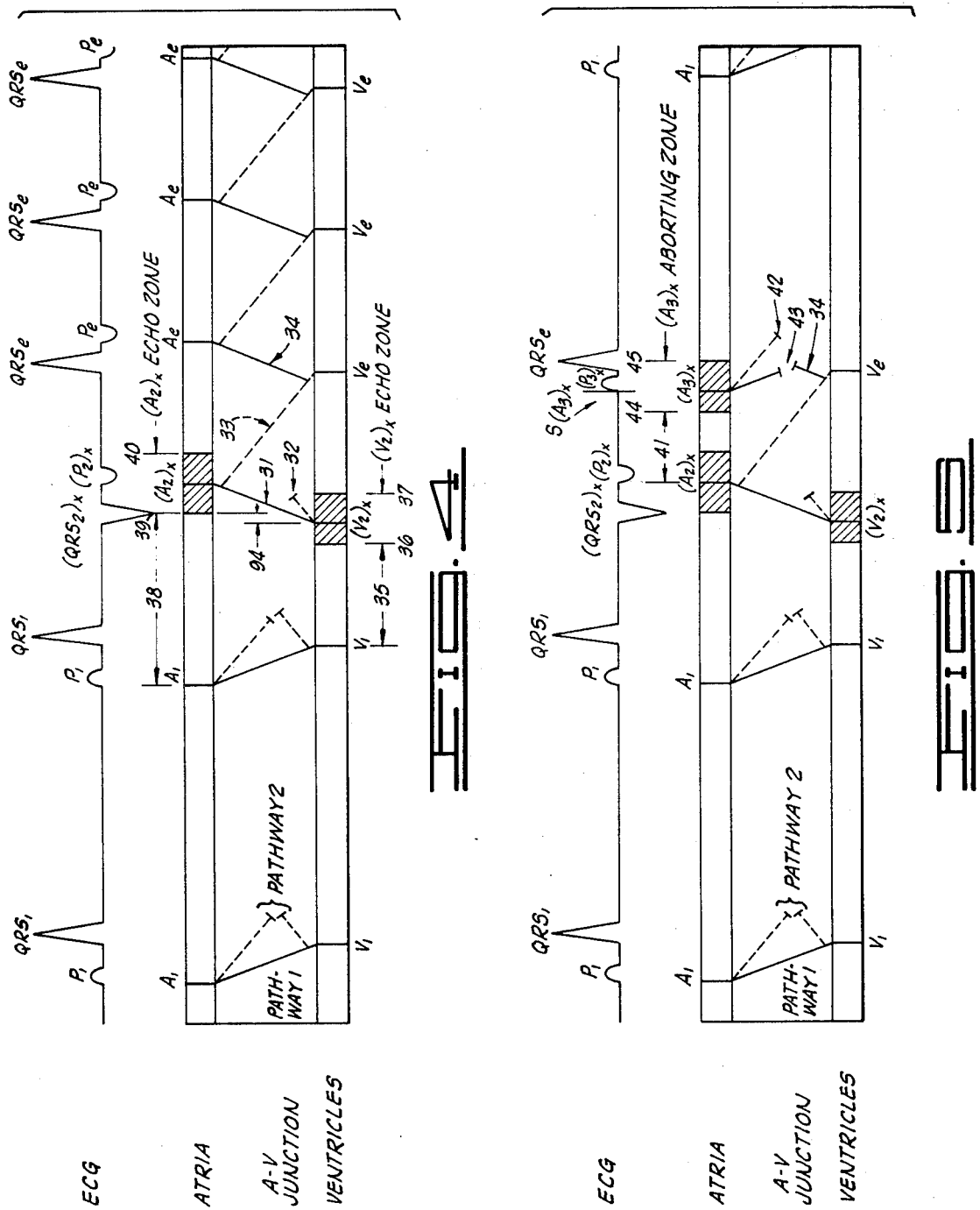

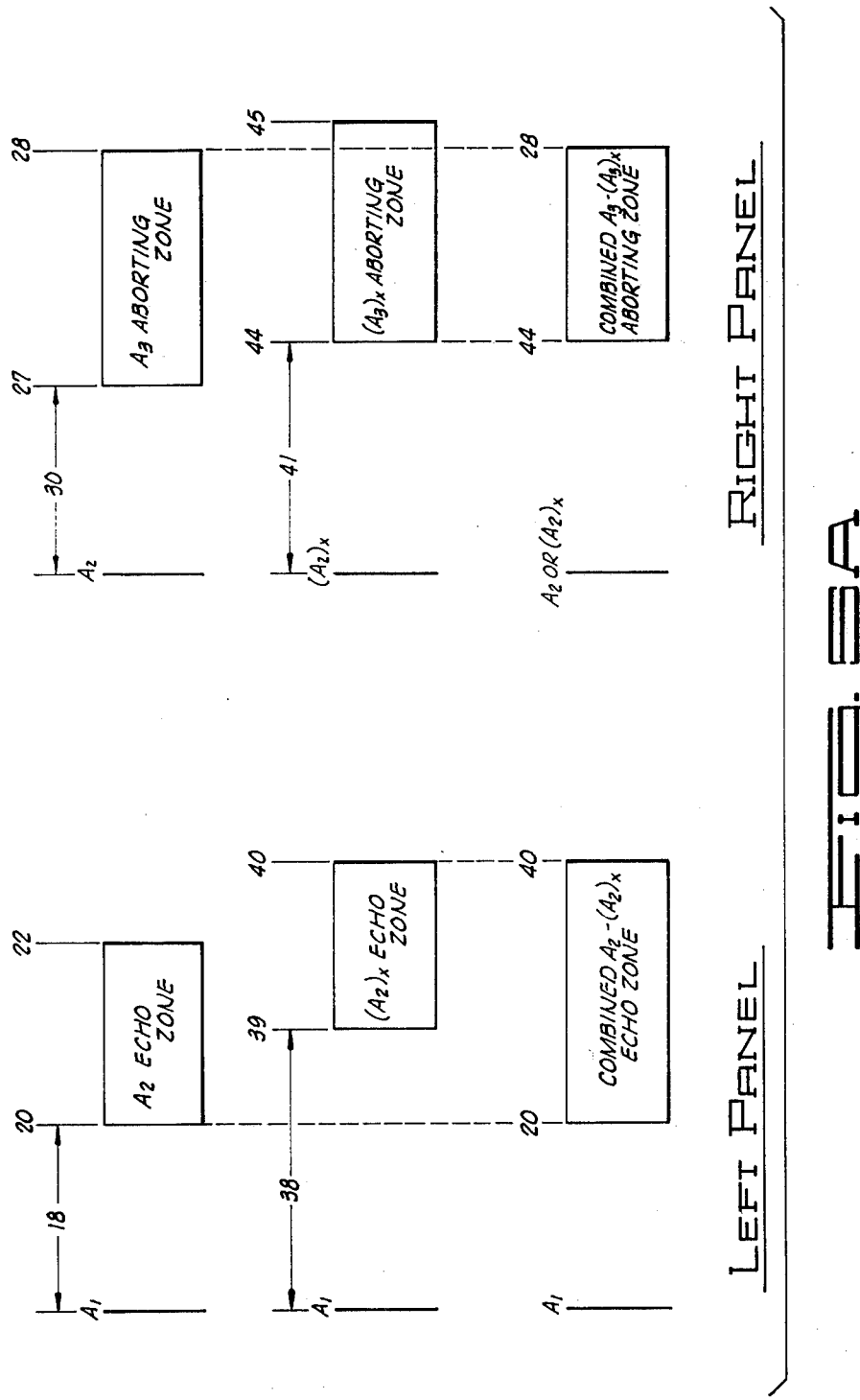

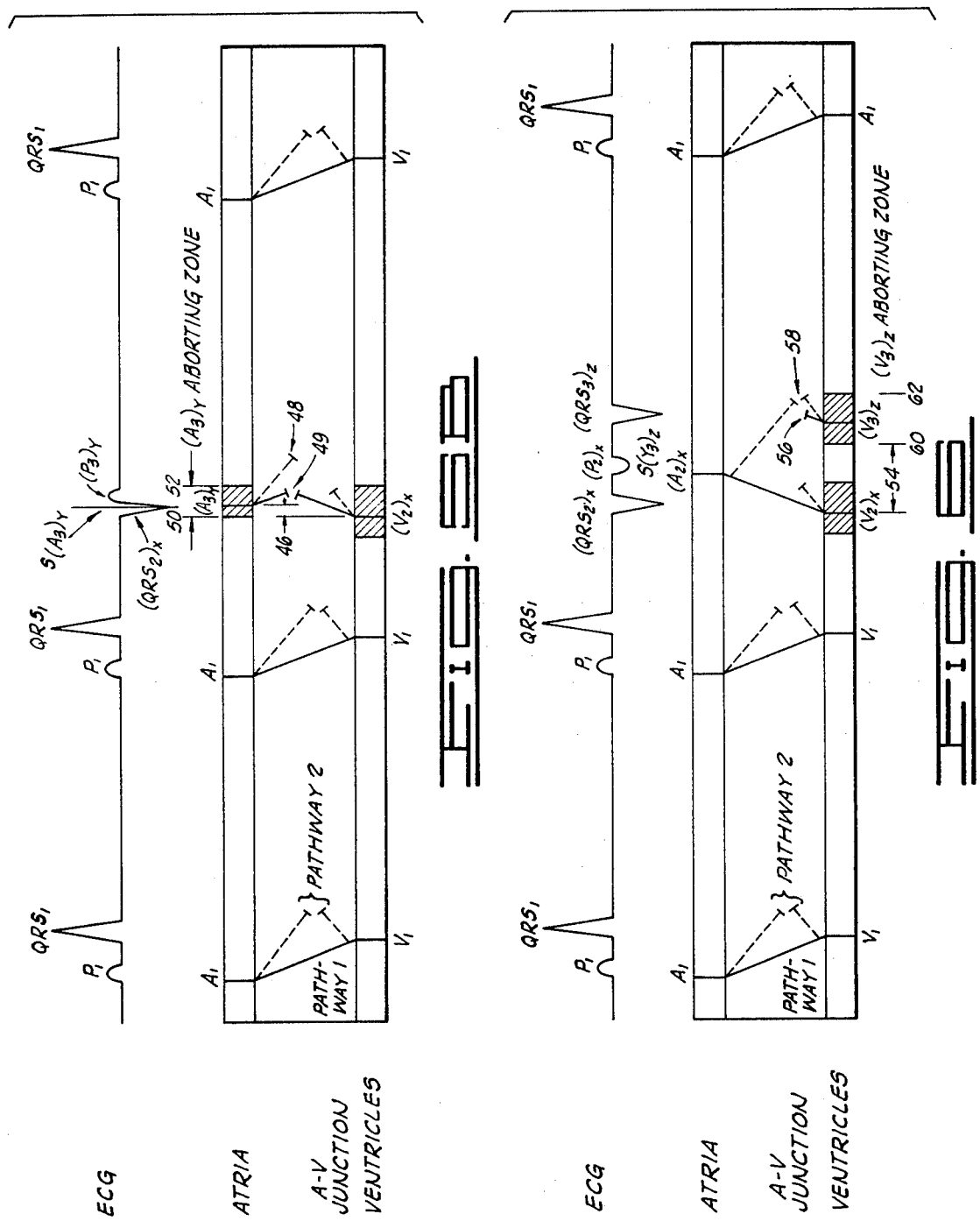

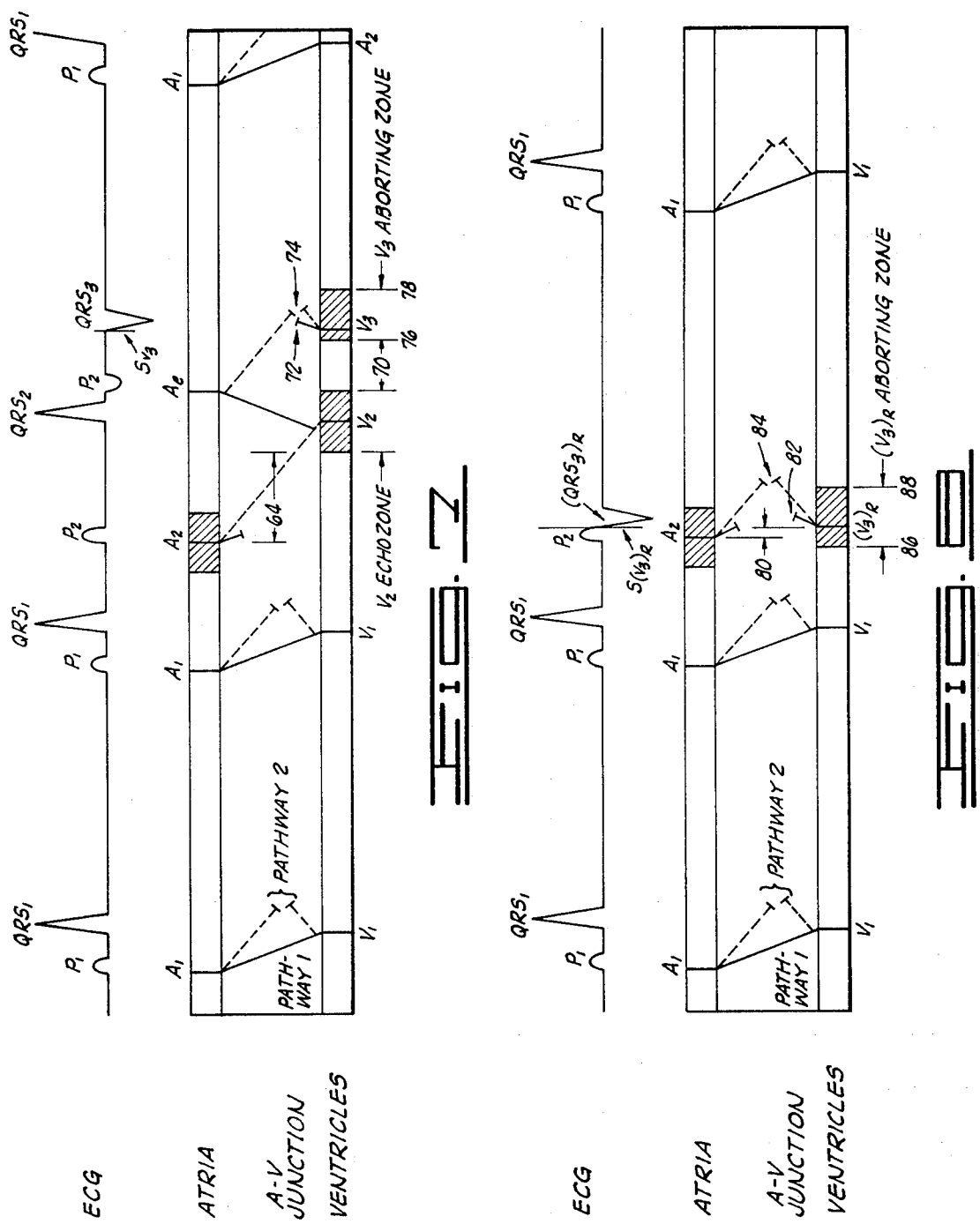

SYSTEM FOR PREVENTION OF PAROXYSMAL SUPRAVENTRICULAR TACHYCARDIA

BACKGROUND OF THE INVENTION

Field of the Invention

The present invention generally contemplates a system for sensing and identifying electrical signals from inciting atrial and/or ventricular electrical impulses which would otherwise result in paroxysmal supraventricular tachycardia [an excessively rapid heart rhythm which can result from either reentry of the electrical impulse within the atrioventricular node or reentry of the electrical impulse between the atria and ventricles using the atrioventricular node for antegrade (atria to ventricles) conduction and an anomalous atrioventricular connection for retrograde (ventricles to atria) conduction] and for delivering critically timed electrical stimuli to the atrial or ventricular cardiac muscle to induce an aborting atrial or ventricular electrical impulse, respectively, for aborting the initiation of such tachycardia.

BRIEF DESCRIPTION OF THE DRAWINGS

FIG. 2, the upper tracing, is a simplified schematic view of an electrocardiogram (ECG) which is a graph of the recording from the body surface (skin) of the electrical signals (potentials) generated by the atrial impulses (P waves), the ventricular impulses (QRS waves) and by the electrical stimuli (S) delivered from the pacemaker controller to the atrial or ventricular cardiac muscle, plotted on the ordinate as a function of time (abscissa). The lower tracing is a schematic drawing referred to in the art as a "ladder diagram" marking the timing of the atrial electrical impulses (shown as vertical lines in the upper box and labeled by the letter A), the ventricular electrical impulses (shown as vertical lines in the lower box and labeled by the letter V), and the middle box (labeled A-V Junction) illustrates the timing of electrical impulses traveling between the atria and ventricles through the first atrioventricular pathway (solid line) and the second atrioventricular pathway (dashed lines). $A_1$ and $P_1$, and $V_1$ and $QRS_1$ represent the normal atrial and ventricular impulses, respectively, initiated in the sinoatrial node. $A_2$ and $P_2$ and $V_2$ and $QRS_2$ represent the inciting atrial impulse and the ventricular impulse resulting from conduction to the ventricles of the inciting atrial impulse, respectively. $A_e$ and $P_e$, and $V_e$ and $QRS_e$ represent atrial echo impulses and ventricular echo impulses, respectively during the dual pathway tachycardia.

FIG. 3 schematically illustrates the timing of the aborting electrical stimulus $S_{A3}$ and the resulting aborting atrial impulse $A_3$ and $P_3$, and the mechanism by which the aborting atrial impulse $A_3$ aborts the initiation of the dual pathway tachycardia. Format same as FIG. 2.

FIG. 4 schematically illustrates the timing of the inciting ventricular impulse $(V_2)_x$ and $(QRS_2)_x$ and atrial impulse $(A_2)_x$ and $(P_2)_x$ resulting from conduction of the inciting ventricular impulse to the atria. Format same as FIG. 2.

FIG. 5 schematically illustrates the timing of the aborting electrical stimulus $S_{(A3)x}$ and the resulting aborting atrial impulse $(A_3)_x$ and $(P_3)_x$ and the mechanism by which the aborting atrial impulse $(A_3)_x$ aborts the initiation of the dual pathway tachycardia. Format same as FIGS. 2 and 4.

FIG. 5A, left panel is a schematic representation of the timing of the $A_2$ echo zone and $(A_2)_x$ echo zone with respect to the last received atrial impulse signal $A_1$ in an individual and illustrates the process whereby the combined $A_2$-$(A_2)_x$ echo zone is created. Right panel is a schematic representation of the timing of the $A_3$ aborting zone with respect to the received inciting atrial impulse signal $A_2$ and the timing of the $(A_3)_x$ aborting zone with respect to the received inciting atrial impulse signal $(A_2)_x$ and illustrates the process whereby the combined $A_3$-$(A_3)_x$ aborting zone is created.

FIG. 5B schematically illustrates the timing of the aborting electrical stimulus $S_{(A3)y}$ and the resulting aborting atrial impulse $(A_3)_y$ and $(P_3)_y$, and the mechanism by which the aborting atrial impulse $(A_3)_y$ aborts the initiation of the dual pathway tachycardia. Format same as FIGS. 2 and 4.

FIG. 6 schematically illustrates the timing of the aborting electrical stimulus $S_{(V3)z}$ and the resulting aborting ventricular impulse $(V_3)_z$, and the mechanism by which the aborting ventricular impulse $(V_3)_z$ aborts the initiation of the dual pathway tachycardia. Format same as FIGS. 2 and 4.

FIG. 7 schematically illustrates the timing of the aborting electrical stimulus $S_{V3}$ and the resulting aborting ventricular impulse $V_3$ and $QRS_3$, and the mechanism by which the aborting ventricular impulse $V_3$ aborts the initiation of the dual pathway tachycardia. Format same as FIG. 2.

FIG. 8 schematically illustrates the timing of the aborting electrical stimulus $S_{(V3)R}$ and the resulting aborting ventricular impulse $(V_3)_R$ and $(QRS_3)_R$, and the mechanism by which the aborting ventricular impulse $(V_3)_R$ aborts the initiation of the dual pathway tachycardia. Format same as FIG. 2.

DESCRIPTION OF THE PREFERRED EMBODIMENTS

Rapid cardiac (heart) electrical rhythm disorders (tachycardias) can result from a variety of mechanisms. The present invention particularly is adapted to abort the onset of a tachycardia which was permitted to be initiated because the heart abnormally contains two pathways for conducting (transmitting) electrical impulses (signals) between the atria and the ventricles and this type of tachycardia is referred to in the art as "paroxysmal supraventricular tachycardia", referred to herein as dual pathway tachycardia.

Figure 1:
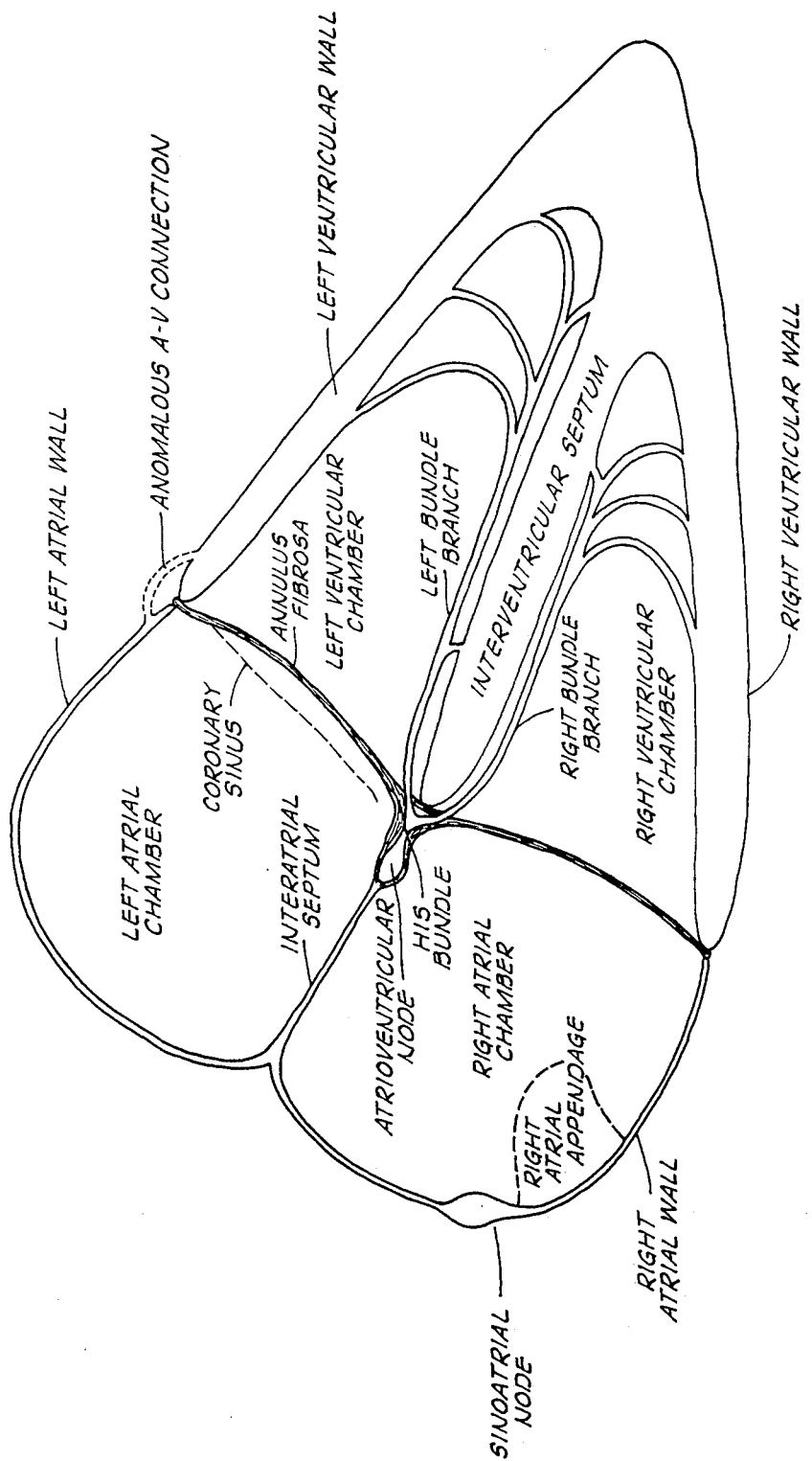
FIG. 1 is a simplified, diagrammatic view of a coronal (frontal plane) section of the heart depicting the locations of the cardiac chambers, the insulating fibrous ring known as the annulus fibrosa, the right atrial appendage, the large cardiac vein lying along the epicardial or outside surface of the posterior or backside of the left atrial wall adjacent to the annulus fibrosa known as the coronary sinus, the specialized cardiac conduction system including the sinoatrial node, the atrioventricular node, the His (or common) bundle, and bundle branches (and their ramifications inserting into the right and left ventricular walls), and one possible location of an anomalous A-V connection. Anomalous A-V connections can bridge the annulus fibrosa along virtually any part of that fibrous ring.

In general and as well known in the art, the human heart generally comprises two upper chambers, the left and right atria, and two lower chambers, the left and right ventricles (FIG. 1), the walls of which are comprised of linearly arranged muscle cells which on receiving an electrical impulse are stimulated (excited) to contract in length as well as to transmit (conduct) the electrical impulse to the previously unstimulated adjacent cells, the net result being the near-simultaneous contraction of all of the muscle cells in the chamber wall producing a reduction in chamber volume which propels some of the chamber's content of blood. The two atria share a common wall (interatrial septum) and function electrically as a single unit. Similarly the two ventricles share a common wall (interventricular septum) and function electrically as a single unit. However, the atria and ventricles are isolated electrically from each other by a ring of connective tissue referred to in the art as the annulus fibrosa which will not conduct an electrical impulse (FIG. 1).

The sinoatrial node is a cluster of specialized cardiac cells located high in the wall of the right atrium near the entrance of the superior vena cava and the sinoatrial node generally, but not always, functions to generate the impulse (signal) for excitation of the entire heart. The electrical impulse initiated in the sinoatrial node is conducted (transmitted) through the atrial cardiac muscle cells causing the atria to contract or "beat". The atrial impulse is then conducted through the atrioventricular node to the ventricles (via the His bundle, bundle branches and peripheral specialized conduction tissue, see FIG. 1) thereby causing the excitation of the cardiac muscle cells in the ventricles causing the ventricles to contract or "beat". In the normal heart, the atrioventricular node is the only pathway for transmitting the atrial electrical impulse to the ventricles.

The atrioventricular node is a composite of interconnected specialized conducting cells and the excitation of these conducting cells by an electrical impulse functions to conduct the impulse to the adjacent unexcited cells. The surface membrane of these conducting cells in the atrioventricular node are polarized when unexcited (not functioning to conduct received impulses) and, when these conducting cells in the atrioventricular node receive an impulse, such conducting cells become depolarized or excited. The current generated by depolarization results in excitation of adjacent cells, and therefore propagation or conduction (transmission) of the impulse. Once these conducting cells in the atrioventricular node have been transformed to the excited state (depolarized), these conducting cells cannot function to receive and conduct a subsequent impulse until the lapse of a predetermined period of time required for the reconditioning of such conducting cells back to the excitable state which includes a return to the polarized state. The period of time required for these conducting cells in the atrioventricular node to become "reconditioned" is referred to in the art as the "refractory period", the refractory period being that period of time during which a second impulse or electrical stimulus cannot produce reexcitation of the cells and propagation (transmission) of the impulse. In addition, the atrioventricular node particularly is adapted to control the time required for an impulse received from the atria to be conducted through the atrioventricular node to the ventricles or, in other words, the atrioventricular node particularly is adapted to delay or dampen the conduction time of an impulse received from the atria if that impulse has been received too close in time with respect to the last received impulse, for example. When the atrioventricular node delays or dampens a received impulse, because that impulse has been received too close in time with respect to the last received impulse, the duration of the refractory period of the conducting cells within the atrioventricular node lengthens. The response to received impulses by atrial and ventricular cardiac cells differs from the response by atrioventricular nodal cells in that the duration of the refractory period of atrial and ventricular cardiac cells shortens as the time between received impulses shortens and little or no delay or dampening of conduction time occurs. These differences in response to impulses received early in time with respect to the last received impulse contribute to the setting of the proper conditions for the dual pathway tachycardias and to the function of this invention.

Shown in FIG. 2 is a schematic of an electrocardiogram (ECG) which is a graph of the electrial potentials or signals generated by depolarization (excitation) of the atrial and ventricular cardiac cells as recorded from the body surface (ordinate) as a function of time (abscissa). Below that tracing is a schematic representation of the timing of the cardiac events which produce the potentials or signals recorded on the electrocardiogram, herein referred to as a "ladder diagram". Atrial (A) and ventricular (V) impulses, represented on the ladder diagram by vertical lines in the boxes labeled "Atria" and "Ventricles", respectively, produce the P waves and QRS waves, respectively, on the electrocardiogram (ECG). Impulses conducted through the atrioventricular (A-V) node, His bundle, bundle branches, and anomalous A-V connections produce potentials or signals too small to be recorded on the standard electrocardiogram and are represented in the box labeled "A-V Junction" on the ladder diagram. Impulses which have been initiated in the normal manner by the sinoatrial node are marked with the suffix 1 (i.e. $A_1$ and $V_1$). The length of time between atrial impulses is referred to as the "atrial cycle length" and the atrial cycle length is diagrammatically represented in FIG. 2 and designated therein by the reference numeral 12. For a human heart beating at a constant rate, the atrial cycle lengths 12 will be equal and constant; however, in practice, the atrial cycle lengths will vary depending upon the activity required of the human heart during the normal functioning of an individual, among other factors. Changes in atrial cycle lengths are accommodated routinely by most human hearts during the human heart's normal functioning lifetime.

In some instances, an atrial impulse, generally originating in the atrial cardiac muscle outside of the sinoatrial node, can occur relatively close in time to the last received atrial impulse and, under the proper conditions, this particular atrial impulse (referred to herein as an "inciting atrial impulse $A_2$") results in a dual pathway tachycardia. An inciting atrial impulse $A_2$ and the resultant ventricular impulse $V_2$ is shown in FIG. 2 and, as shown in FIG. 2, the inciting atrial impulse $A_2$ occurs within a short period of time after an atrial impulse $A_1$ and prior to the time when another atrial impulse $A_1$ would have occured had the established atrial cycle length been followed. As illustrated in FIG. 2, the second atrial and ventricular impulses $A_1$ and $V_1$ are shown followed by an inciting atrial impulse $A_2$ with its resultant ventricular impulse $V_2$, and the atrial and ventricular impulses, $A_1$ and $V_1$, which would have occured at a time equal to the predetermined atrial cycle length 12 after the second atrial and ventricular impulses $A_1$ and $V_1$ are shown in dotted lines. The particular atrial and ventricular impulses $A_1$ and $V_1$ (and the corresponding $P_1$ and $QRS_1$ waves on the ECG) are shown in dotted lines in FIG. 2 to indicate that these particular $A_1$ and $V_1$ impulses in fact do not occur and these particular dotted line atrial and ventricular impulses $A_1$ and $V_1$ are shown simply to graphically illustrate the positioning of the inciting impulse $A_2$.

Devices have been constructed in the past to provide electrical stimulation of the atrial and/or ventricular cardiac muscle when an individual's heart fails to produce the required impulses to cause normal atrial and ventricular beating, such devices commonly being referred to in the art as "pacemakers". In general, pacemakers have included a controller which was connected to the atrial and/or ventricular cardiac muscle by way of an electrical conduit(s) and the controller functioned to provide electrical stimuli at predetermined intervals through the electrical conduit(s) to the atrial and/or ventricular cardiac muscle for stimulating an atrial and/or ventricular impulse at a given or predetermined rate or frequency. The electrical stimulus or impulse provided by the controllers in prior pacemakers generally has been either of a constant current or a constant voltage type of electrical impulse depending upon the design of the particular pacemaker. Further, some prior pacemakers have been constructed to sense the signal of the atrial and/or ventricular cardiac muscle impulse and to provide a stimulating electrical impulse only when a spontaneous impulse signal is not sensed. One modification of such devices allows the delivery of a stimulating electrical impulse to the ventricles at a predetermined interval after each sensed atrial signal to preserve the normal relationship between the atrial and ventricular impulses wherein a ventricular impulse follows each atrial impulse by a predetermined delay period of time, the delay period of time being relatively short in comparison to the atrial cycle length interval 12 (the two pacing modalities incorporating this modification are referred to in the art as the Atrial-Synchronous/Ventricular-Inhibited or VDD mode of pacing and the A-V Universal or DDD mode of pacing). Another modification allows the recognition of an abnormally rapid rhythm or tachycardia (by heart rate criteria, among others) following which the pacemaker delivers a predetermined number of electrical stimuli at predetermined intervals to the atrial and/or ventricular cardiac muscle for terminating the established tachycardia. Also, it should be noted that the electrical conduit(s) between the controller and the cardiac muscle in the prior pacemakers have been attached to: (1) the endocardial (inside surface of the right atrium (generally near the right atrial appendage high in the right atrium near the sinoatrial node); (2) the endothelial (inside) surface of the coronary sinus (large vein adjacent to the epicardial or outside surface of the base of the left atrium along the margin of the annulus fibrosa); (3) the endocardial (inside) surface of the right ventricle (generally near its apex); and (4) to the apicardial (outside) surface of the left and right atria and left and right ventricles. The prior pacemakers have not been specifically constructed to sense and identify the inciting impulses and, thus, the prior pacemakers have not been constructed specifically to prevent (abort) the initiation of the dual pathway tachycardias which follow inciting impulses. Atrial-Synchronous/Ventricular-Inhibited (VDD) and A-V Universal (DDD) pacemakers have been adapted to prevent (abort) the initiation of the dual pathway tachycardias by sensing *all* atrial impulse signals and delivering an electrical stimulus to the ventricular cardiac muscle at some predetermined interval of time following each sensed atrial impulse signal to induce a ventricular impulse sufficiently early in time with respect to the preceding atrial impulse to prevent the delay in conduction time between the inciting atrial impulses $A_2$ and their resultant ventricular impulses $V_2$ which is necessary for the initiation of the dual pathway tachycardias; however, the usefulness of these pacing modalities in preventing (aborting) the initiation of the dual pathway tachycardias has been limited, at least in the experience of the inventors of the system of the present invention. The present invention provides an improved system for identifying inciting atrial impulses $A_2$ and for delivering an aborting electrical stimulus $S_{A3}$ to the atrial cardiac muscle to induce an aborting atrial impulse $A_3$ in response to a sensed inciting atrial impulse signal $A_2$ which will abort the onset of the dual pathway tachycardia which otherwise would have occured following the inciting atrial impulse $A_2$.

There are two conditions which may exist in an individual which are presently known and which are susceptible to the dual pathway tachycardias induced as a result of an inciting atrial impulse $A_2$. These two conditions are referred to in the art as atrioventricular nodal reentry and atrioventricular reentry using an accessory atrioventricular pathway (or anomalous A-V connection) for retrograde conduction. As mentioned before, there generally is only one structure, the A-V node, for conducting an atrial impulse to the ventricles and, that structure functions as a single pathway. Common to both of these last mentioned conditions, the heart contains two pathways over which impulses may be conducted (transmitted) between the atrial and ventricular cardiac muscle. The two pathways may both be confined to the atrioventricular node (referred to in the art as dual atrioventricular pathways) or the second pathway may result from the presence of a small strand of cardiac muscle located outside of the atrioventricular node which bridges the annulus fibrosa, electrically connecting the atrial and ventricular cardiac muscle. This latter structure is referred to in the art as an anomalous A-V connection or as an accessory A-V pathway and is schematically represented in FIG. 1 in dashed lines.

Figure 9:
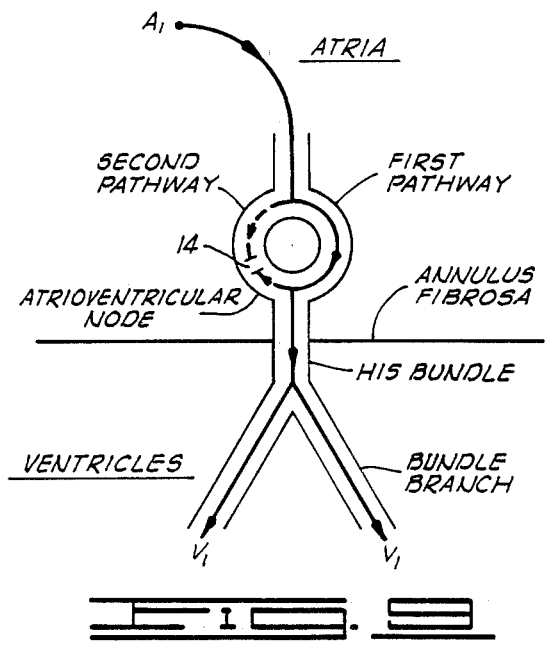
FIG. 9 is a schematic, diagrammatic view of a portion of a heart illustrating the condition wherein an atrial impulse $A_1$ is conducted from the atria to the ventricles through the atrioventricular node in such a manner that a dual pathway tachycardia will not be induced. As in earlier figures, conduction of an impulse through the first pathway is represented by a solid line and conduction of an impulse through the second pathway is represented by a dashed line. In general, the conduction time of an impulse through the length of the second pathway is longer than the conduction time of an impulse through the length of the first pathway.
Figure 10:
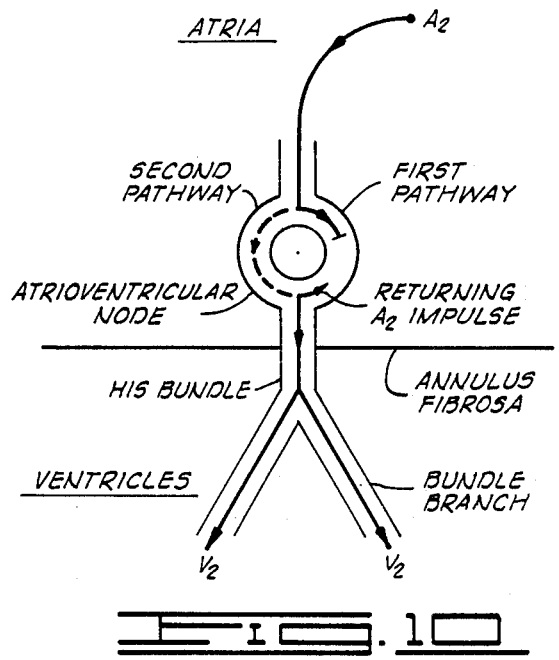
FIG. 10 is a schematic, diagrammatic view, similar to FIG. 9, but illustrating the condition of an inciting atrial impulse $A_2$ being conducted through the atrioventricular node in a manner which will result in a dual pathway tachycardia.
Figure 11:
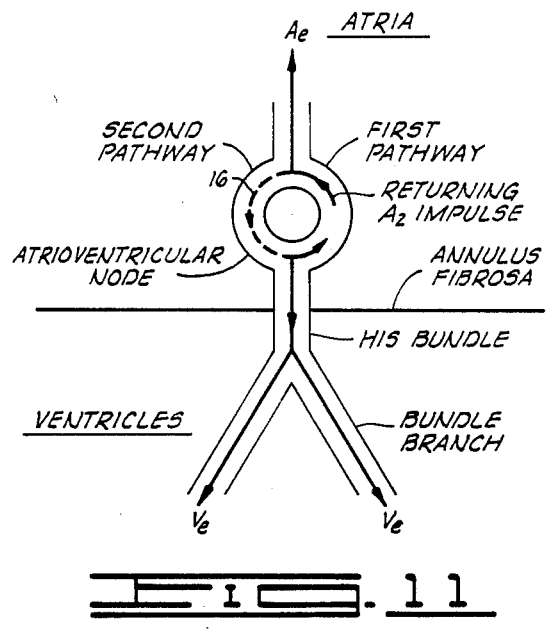
FIG. 11 is a schematic, diagrammatic view, similar to FIGS. 9 and 10, but illustrating the condition at a point in time later than FIG. 10 in which the inciting atrial impulse $A_2$ being conducted through the atrioventricular node has returned towards the atria producing an atrial echo impulse $A_e$, then returned towards the ventricles producing a ventricular echo impulse $V_e$, and is again returned towards the atria establishing the pattern for a dual pathway tachycardia.

The condition referred to as atrioventricular nodal reentry is diagrammatically illustrated in FIGS. 9, 10, and 11. With respect to this condition, the atrioventricular node functions as two separate conducting pathways connected at the top of the atrioventricular node near the atria and connected at the bottom of the atrioventricular node near the His bundle and ventricles, the two atrioventricular nodal pathways being designated in FIGS. 9, 10, and 11 as a first pathway and a second pathway for conducting electrical impulses between the atria and the ventricles. In FIGS. 2, 3, 4, 5, 5B, 6, 7, 8, 9, 10, and 11, conduction through the first pathway is represented by a solid line and conduction through the second pathway is represented by a dashed line. In general, but not always, the conduction time of an impulse being conducted through the length of the second pathway is longer than the conduction time of an impulse being conducted through the length of the first pathway. With respect to atrioventricular nodal reentry, when an atrial impulse $A_1$ is received by the atrioventricular node and when the conducting cells in both the first and second pathways are excitable (i.e. have been reconditioned to receive and conduct an electrical impulse), the received atrial impulse $A_1$ is conducted through both the first and second pathways toward the ventricles, this situation being illustrated in FIG. 9 and in the first and second set of atrial and ventricular impulses $A_1$ and $V_1$ in FIG. 2. The impulse being conducted through the first pathway arrives at the junction of the first and second pathways before the impulse traveling through the second pathway, and that first pathway impulse penetrates the lower end of the second pathway and attempts to conduct through the second pathway toward the atria. The two impulses traveling in opposite directions through the second pathway collide, terminating both impulses because each of the two impulses encounters cells which have just been depolarized and have not had sufficient time to become reconditioned for accepting and conducting another impulse. The two impulses being conducted in opposite directions through the second pathway are illustrated by dashed lines in FIGS. 2 and 9 and the termination (block) of both impulses resulting from their collision is illustrated by the short lines drawn perpendicular to the dashed lines and marked by the reference numeral 14, similar termination marks being illustrated elsewhere in FIGS. 2, 3, 4, 5, 5B, 6, 7, 8, 10, 12, 13, 14, and 16 indicating blockage (termination) of the impulse(s) but not being specifically designated with a reference numeral. Thus, the atrial impulse $A_1$ being conducted towards the ventricles through the second pathway is blocked from reaching the His bundle (and therefore the ventricles) and the atrial impulse $A_1$ originally conducted through the first pathway is blocked from conducting back towards the atrial through the second pathway. Under these conditions and as illustrated in the first two complexes for FIG. 2 and in FIG. 9, the atrial impulse $A_1$ is conducted through the atrioventricular node to the ventricles by way of the first pathway and yet the atrial impulse $A_1$ being conducted through the first pathway is blocked from conducting back to the atria through the second pathway because the conducting cells in the second pathway still are inexcitable (not yet reconditioned to receive and conduct an impulse). It should be noted that it is also true, with respect to the situation illustrated in FIG. 9, that the atrial impulse $A_1$ traveling through the second pathway is blocked from conducting back to the atria through the first pathway because the conducting cells in the first pathway likewise still are inexcitable. Thus, with respect to the condition illustrated in FIG. 9, the atrial impulse $A_1$ is conducted to the ventricles without detrimental incident.

If an early atrial impulse is received by the atrioventricular node at a time when the conducting cells in both the first and second pathways are still inexcitable (not yet reconditioned) following the last received atrial impulse $A_1$, such an atrial impulse simply is blocked from conducting through either the first or the second pathway. An atrial impulse received at the atrioventricular node at this time when both the first and second pathways are still inexcitable simply will be blocked and such a received atrial impulse will not result in a dual pathway tachycardia and will not result in an atrial impulse being conducted through the atrioventricular node to the ventricles. This early received atrial impulse, assuming one received at various odd times, does not function to cause any beating of the ventricles and does not function to cause any problem relating to a dual pathway tachycardia. This type of early atrial impulse is not considered to be an inciting atrial impulse $A_2$ as that term is used in the present description.

Since the refractory periods (time period after depolarization or excitation of the cells required for reconditioning of the cells to allow the cells to receive, become reexcited, and conduct or transmit another impulse) of the first and second pathways may differ in duration, there may be a time with respect to the last received atrial impulse $A_1$ at which the conducting cells in the first pathway may still be refractory to stimulation (be inexcitable) while the conducting cells in the second pathway may become excited or depolarized. These two time periods of refractoriness of the two pathways may be so timed with respect to a received atrial impulse $A_2$ as to create a condition wherein, when an atrial impulse $A_2$ is received by the atrioventricular node, the conducting cells in the first pathway are still refractory (not yet reconditioned following depolarization from the atrial impulse $A_1$) while the conducting cells in the second pathway have already become excitable (reconditioned). In this instance a received atrial impulse $A_2$ will be conducted through the second pathway to the ventricles while simultaneously the same atrial impulse $A_2$ will be blocked in the first pathway. Under these circumstances and if the timing of conduction through the second pathway is such that, when the atrial impulse $A_2$ exits from the second pathway at the junction of the two pathways near the ventricles, the conducting cells in the first pathway have recovered excitability (been reconditioned), then the impulse resulting from the received atrial impulse $A_2$ will exit from the second pathway, be conducted to the ventricles (via the His bundle) and be conducted back towards the atria through the first pathway (via the junction of the two pathways near the ventricles), the conducting cells in the first pathway being reconditioned. The transmission of the $A_2$ impulse back towards the atria through the first pathway will result in an additional atrial impulse referred to herein and in the art as an atrial echo impulse $A_e$.

This last described condition resulting in the atrial echo impulse $A_e$ is illustrated in FIGS. 2, 10, and 11. As shown in FIG. 10, the early inciting atrial impulse $A_2$ is initially blocked from being conducted through the first pathway, but is conducted through the second pathway to the ventricles and this inciting atrial impulse $A_2$ is further transmitted from the second pathway to the first pathway via the junction of the two pathways near the ventricles. As shown in FIG. 11, the inciting atrial impulse $A_2$ has been conducted backwards through the first pathway to the atria to provide the echo impulse $A_e$. If the impulse traveling back towards the atria over the first pathway arrives at the junction of the two pathways near the atria at a time when the cells of the second pathway have recovered excitability (been reconditioned), then the impulse may reenter the second pathway and be conducted towards the ventricles through the second pathway, this last mentioned conduction through the second pathway being shown in dashed lines and marked by the reference numeral 16 in FIGS. 2 and 11. The result of the perpetual reentering of the impulse between the first and second pathways at their two junctions is one form of dual pathway tachycardia referred to herein and in the art as atrioventricular nodal reentry.

In summary, an inciting atrial impulse $A_2$ is an atrial impulse which is received by the conducting cells in the atrioventricular node at a time when the conducting cells in one of the first and second pathways (the second pathway for example) are reconditioned or excitable (receptive) while the conducting cells in the other one of the first and second pathways (the first pathway for example) are still refractory to excitation, and at a time such that the conducting cells in the initially blocked first or second pathway (the first pathway for example) will be reconditioned for conducting the impulse from the initially conducting pathway (the second pathway for example) back towards the atria through the intially blocked pathway (the first pathway for example). Thus, with respect to atrioventricular nodal reentry as illustrated in FIGS. 2, 9, 10, and 11, an inciting atrial impulse $A_2$ is an impulse which is received at the atrioventricular node under the following conditions: (1) when the conducting cells in one of the first and second pathways (the second pathway for example) are excitable (receptive); (2) when the conducting cells in the other of the first and second pathways (the first pathway for example) are still refractory (unreceptive) and block any received impulse; (3) when the initially refractory conducting cells in the first or second pathway (the first pathway for example) will be reconditioned (excitable) in time to receive and conduct the impulse arriving at the junction of the two pathways near the ventricles as a result of conduction of the inciting atrial impulse $A_2$ through the initially conducting first or second pathway (the second pathway for example) toward the ventricles; and (4) when the conducting cells in the initially conducting first or second pathway (the second pathway for example) will be reconditioned in time to receive and conduct the impulse arriving at the junction of the two pathways near the atria as a result of conduction of the impulse towards the atria over the initially refractory first or second pathway (the first pathway for example) towards the ventricles, forming a repetitive circuit.

The condition just described with respect to atrioventricular nodal reentry also exists in individuals having a condition known as atrioventricular reentry using an accessory A-V pathway (or anomalous A-V connection) for retrograde conduction, and this particular condition is diagrammatically and schematically illustrated in FIGS. 2, 13, 14, and 15.

With respect to this condition, the atrioventricular node functions in a "normal" manner to provide a single pathway for conducting received impulses between the atria and ventricles. However, with respect to atrioventricular reentry using an accessory atrioventricular (A-V) pathway for retrograde conduction, the heart has an anomalous strand of conductive cells which extends around the annulus fibrosa to form another pathway capable of conducting impulses between the atria and the ventrices, and this strand, referred to in the art as an anomalous atrioventricular (A-V) connection or accessory A-V pathway is diagrammatically illustrated by the dotted lines in FIG. 1. In FIGS. 2, 13, 14, and 15 and in the discussion below, the accessory A-V pathway is referred to as the "first pathway" and conduction through the accessory A-V pathway is represented by a solid line, and the atrioventricular node is referred to as the "second pathway" and conduction through the atrioventricular node is represented by dashed lines. In general, the conduction time of an impulse being conducted through the length of the atrioventricular node (second pathway) is longer than the conduction time of an impulse being conducted through the length of the accessory A-V pathway (first pathway).

Figure 13:
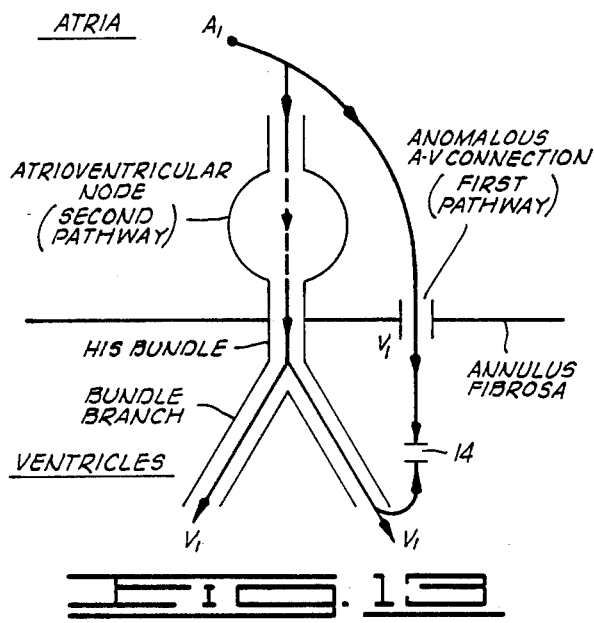
FIG. 13 is a schematic, diagrammatic view of a portion of a heart illustrating the condition of an anomalous atrioventricular connection (or accessory atrioventricular pathway) which provides another conduction pathway between the atria and ventricles in addition to the atrioventricular node which functions normally to provide a single conduction pathway between the atria and ventricles and illustrating the condition wherein the atrial impulse $A_1$ is conducted from the atria to the ventricles through both pathways in such a manner that a dual pathway tachycardia will not be induced. Conduction of an impulse through the anomalous atrioventricular connection is represented by a solid line and conduction of an impulse through the atrioventricular node is represented by a dashed line. In general, the conduction time of an impulse through the length of the atrioventricular node is longer than the conduction time of an impulse through the length of the anomalous atrioventricular connection.
Figure 14:
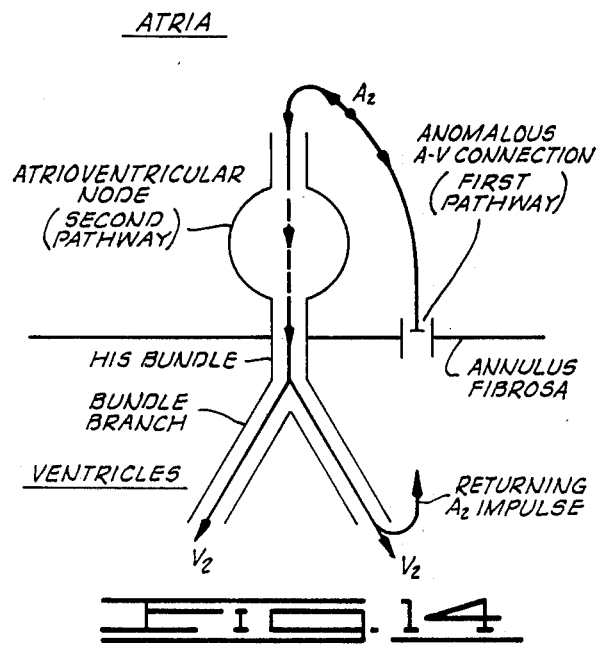
FIG. 14 is a schematic, diagrammatic view, similar to FIG. 13, but illustrating the condition of an inciting atrial impulse $A_2$ being conducted through the atrioventricular to the ventricles in a manner which will result in a dual pathway tachycardia.

With respect to atrioventricular reentry using an accessory atrioventricular pathway for retrograde conduction and referring particularly to FIG. 13 and the first two complexes in FIG. 2, when an atrial impulse $A_1$ is received from the atria by both the first and second pathways, and when the conducting cells in both the first and second pathways are excitable, the received atrial impulse $A_1$ is conducted through both the first and second pathways to the ventricles. The impulse being conducted through the first pathway (solid line) also encounters the conducting cells in the second pathway and attempts to conduct the impulse to the conducting cells in the second pathway; however, since the conducting cells in the second pathway have just been depolarized and are therefore refractory to reexcitation, the impulse from the first pathway is blocked from entering the second pathway, this situation being illustrated diagrammatically in FIGS. 2 and 13 and being marked by the reference numeral 14. In a like manner, the atrial impulse $A_1$ being conducted through the second pathway is blocked from entering the first pathway because the conducting cells in the first pathway likewise have just been depolarized and are therefore refractory to reexcitation. Under these conditions and as illustrated in FIG. 13 and the first two complexes of FIG. 2, the atrial impulse $A_1$ is conducted from the atria to the ventricles through both the first and second pathways without detrimental incident, in a manner like that described before with respect to FIG. 9.

If an atrial impulse $A_1$ is received at a time when the conducting cells in both the first and second pathways are still refractory, such an atrial impulse $A_1$ simply is blocked from traversing either the first or second pathway. A received atrial impulse $A_1$ so timed will not result in a dual pathway tachycardia and will not result in an atrial impulse $A_1$ being conducted from the atria to the ventricles, and such an early received atrial impulse $A_1$ is not considered to be an inciting atrial impulse $A_2$ as that term is used herein.

Figure 15:
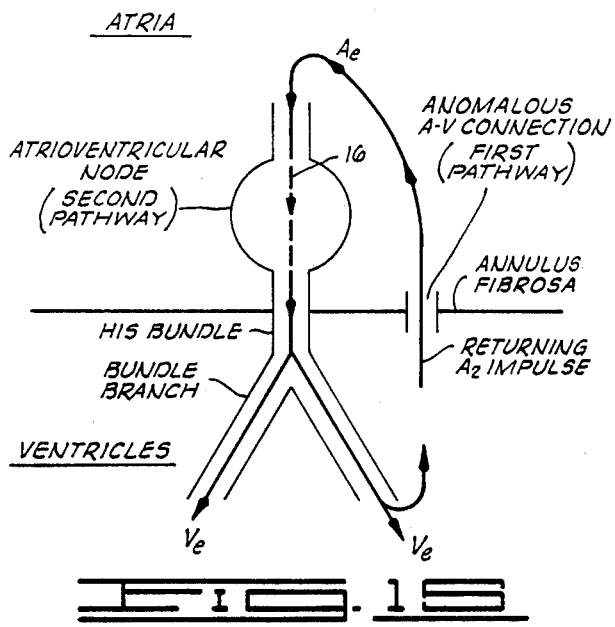
FIG. 15 is a schematic, diagrammatic view, similar to FIGS. 13 and 14, but illustrating the condition at a point in time later than FIG. 14 in which the inciting atrial impulse $A_2$ being conducted through the atrioventricular node to the ventricles has returned to the atria through the anomalous atrioventricular connection producing an atria echo impulse $A_e$, then returned to the ventricles through the atrioventricular node producing a ventricular echo impulse $V_e$, and is preparing to return to the atria establishing the pattern for a dual pathway tachycardia.

In a manner like that described before with respect to atrioventricular nodal reentry, the conducting cells in the first pathway and the conducting cells in the second pathway may have refractory periods (time period following the last received atrial impulse $A_1$ during which the conducting cells cannot be reexcited), of differing durations and these two durations of refractoriness may be so timed as to create a condition wherein, when an atrial impulse $A_2$ is received, the conducting cells in one of the first or second pathways (the second pathway for example) are excitable (receptive) while the conducting cells in the other one of the first or second pathways (the first pathway for example) still are refractory (unreceptive). In this instance and assuming the conducting cells in the first pathway are still refractory while the conducting cells in the second pathway have already become excitable, a received atrial impulse $A_2$ will be conducted through the second pathway to the ventricles while simultaneously the same atrial impulse $A_2$ will be blocked from being conducted through the first pathway, this condition being illustrated in FIGS. 14 and the third complex in FIG. 2. Under these circumstances and if the timing of conduction through the second pathway is such that when the atrial impulse $A_2$ exits from the second pathway and attempts to be conducted back towards the atria through the first pathway, the conducting cells in the first pathway have been reconditioned, then the impulse resulting from such a received atrial impulse $A_2$ will pass from the second pathway and be conducted back to the atria through the first pathway, thereby resulting in an additional atrial impulse referred to herein and in the art as an atrial echo impulse $A_e$. This last described condition resulting in the atrial echo impulse $A_e$ is illustrated in FIGS. 2 and 15. If the atrial echo impulse $A_e$ arrives at the second pathway at a time when the cells of the second pathway have recovered excitability (been reconditioned), then the atrial echo impulse $A_e$ may reenter the second pathway and be conducted to the ventricles through the second pathway, this last mentioned conduction through the second pathway being shown in dashed lines and marked by the reference numeral 16 in FIGS. 2 and 15. The result of the perpetual reentering of the impulse between the first and second pathways is one form of dual pathway tachycardia referred to as atrioventricular reentry using an accessory A-V pathway for retrograde conduction.

Thus, with respect to the atrioventricular reentry using an accessory atrioventricular pathway for retrograde conduction illustrated in FIGS. 2, 13, 14, and 15, an inciting atrial impulse $A_2$ is one which is received from the atria under the following conditions: (1) when the conducting cells in the second pathway are excitable (receptive); (2) when the conducting cells in the first pathway are still refractory (unreceptive); (3) when the initially refractory conducting cells in the first pathway will be reconditioned (excitable) in time to receive and conduct the impulse arriving at the ventricular side of the first pathway as a result of conduction of the inciting atrial impulse $A_2$ through the initially conducting second pathway, back to the atria to produce an atrial echo impulse $A_e$; and (4) when the conducting cells in the initially conducting second pathway will be reconditioned in time to receive and conduct the atrial echo impulse $A_3$ back to the ventricles forming a repetitive circuit.

Some accessory atrioventricular pathways are capable of conduction only in the retrograde direction (i.e. from ventricles to atria). In this instance, all atrial impulses are blocked from traversing the accessory atrioventricular pathway to the ventricles. With respect to this condition an atrial impulse is an inciting atrial impulse $A_2$ when conditions 1, 3, and 4 of the previous paragraph are fulfilled.

Thus, with respect to the atrioventricular nodal reentry (diagrammatically and schematically illustrated in FIGS. 9, 10, and 11) and with respect to the atrioventricular reentry using the accessory atrioventricular pathway for retrograde conduction (illustrated in FIGS. 13, 14, and 15), an inciting atrial impulse $A_2$ is an atrial impulse which occurs at a time after the conducting cells in the second pathway have been reconditioned to conduct an impulse and at a time when the conducting cells in the first pathway still are refractory to excitation, and at a time such that, when the impulse resulting from the initial inciting atrial impulse $A_2$ is conducted through the second pathway to the junction of the first and second pathways near the ventricles, the conducting cells in the first pathway have been reconditioned to receive and conduct this impulse back towards the atria thereby producing an atrial echo impulse $A_e$ and at such a time so that, when the atrial echo impulse $A_e$ is received by the conducting cells in the second pathway, the conducting cells in the second pathway have had sufficient time to be reconditioned for receiving and conducting this atrial echo impulse $A_e$ back towards the ventricles initiating a condition of sustained reentering of the second pathway in the antegrade direction (atria to ventricles) and the first pathway in the retrograde direction (ventricles to atria).

Thus, there is a period of time between a received atrial impulse $A_1$ and a time when an inciting atrial impulse $A_2$ might occur and this period of time is diagrammatically illustrated in FIG. 2 and designated therein by the reference numeral 18. The period of time 18 is the longer of the atrial refractory period (period of time following the prior atrial impulse $A_1$ during which the atria cannot be reexcited) or the period of time following the last received atrial impulse $A_1$ during which the conducting cells in both the first and the second pathways still are refractory (not yet reconditioned to receive and conduct the atrial impulse) and an atrial impulse received during this period of time 18 simply will be blocked in both first and second pathways, the stop time of this period 18 is designated in FIG. 2 by the reference numeral 20.

In addition, there is a time after the receipt of an atrial impulse $A_1$ after which another received atrial impulse will not constitute an inciting atrial impulse $A_2$ because either: (1) the conducting cells in both the first and second pathways are reconditioned (receptive) and an atrial impulse received within this period of time simply will be conducted through both the first and second pathways in a "normal" manner (as illustrated in FIGS. 9 and 13); or (2) the atrial impulse is received sufficiently early in time with respect to the preceding atrial impulse $A_1$ that the cells in the first pathway still are refractory to excitation and the cells in the second pathway have recovered excitability (been reconditioned) allowing conduction to the ventricles only through the second pathway, but not sufficiently early to produce the degree of conduction delay in the second pathway (dampening effect) necessary to allow the cells in the first pathway to recover excitability to allow the impulse initially conducted through the second pathway to be conducted back towards the atrial through the first pathway. This time after which an inciting atrial impulse $A_2$ will not occur is shown in FIG. 2 and designated therein by the reference numeral 22. The time period between the time 20 and the time 22 is defined herein as the "$A_2$ echo zone", the time 20 sometimes being referred to herein as the start time of the $A_2$ echo zone and the time 22 sometimes being referred to herein as the stop time of the $A_2$ echo zone. Thus, the $A_2$ echo zone is the time period beginning at a time before which an inciting atrial impulse $A_2$ could not occur (time 20) and ending at a time after which an inciting atrial impulse $A_2$ could not occur (time 22). An atrial impulse received within the $A_2$ echo zone is defined herein as an inciting atrial impulse $A_2$ which will result in a dual pathway tachycardia absent some intervention to abort the oncoming dual pathway tachycardia.

Figure 12:
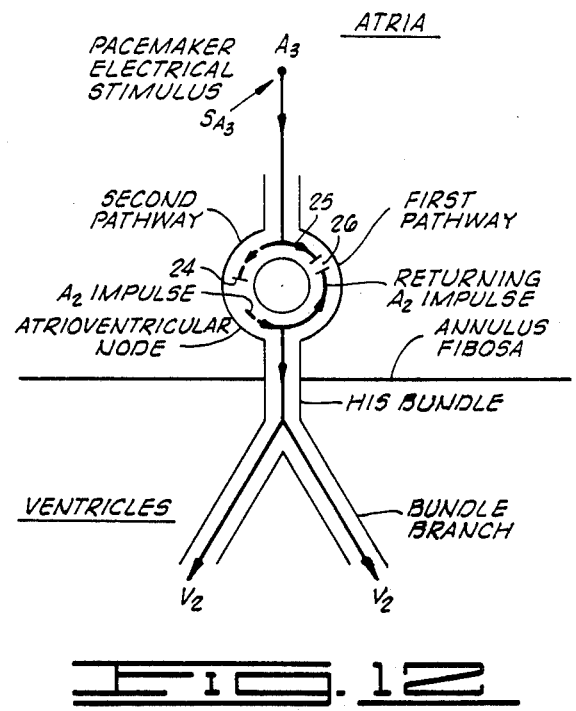
FIG. 12 is a schematic, diagrammatic view similar to FIGS. 9, 10, and 11 and illustrating the condition at a point in time similar to the time of FIG. 10 wherein after an inciting atrial impulse $A_2$ is received by the atrioventricular node, the pacemaker controller delivers to the atrial cardiac muscle an aborting electrical stimulus $S_{A3}$ which induces an aborting atrial impulse $A_3$ which is conducted to the atrioventricular node and functions to abort the initiation of the dual pathway tachycardia.
Figure 16:
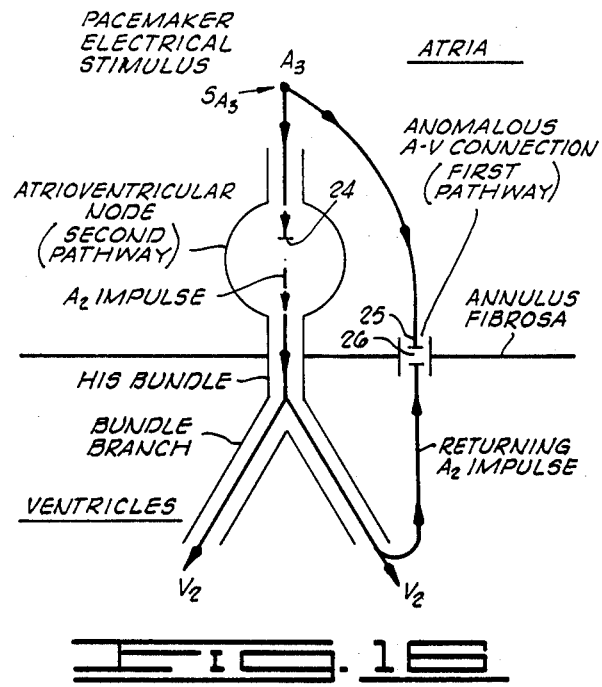
FIG. 16 is a schematic, diagrammatic view similar to FIGS. 13, 14, and 15 and illustrating the condition at a point in time similar to the time of FIG. 14 wherein, after an inciting atrial impulse $A_2$ is received by the atrioventricular node, the pacemaker controller delivers to the atrial cardiac muscle an aborting electrical stimulus $S_{A3}$ which induces an aborting atrial impulse $A_3$ which is conducted to the atrioventricular node and anomalous atrioventricular dual pathway tachycardia.

Initially, it is necessary that the $A_2$ echo zone be defined in terms of the times from the last received atrial impulse $A_1$ or, in other words, it initially is necessary to define the times 20 and 22 with respect to the last received atrial impulse $A_1$ (diagrammatically illustrated in FIG. 2), thereby defining the $A_2$ echo zone, the $A_2$ echo zone being a time range within which an inciting atrial impulse $A_2$ may occur after an atrial impulse $A_1$. Once the $A_2$ echo zone is defined, the impulses or signals produced in the atrial cardiac muscle are sensed by the controller of a pacemaker by way of the interconnecting electrical conduit. Thus, the controller now can sense the signals of the impulses in the atrial cardiac muscle and, when an atrial impulse signal is received at a time falling within the $A_2$ echo zone, this atrial impulse is identified and determined to be an inciting atrial impulse $A_2$. Since the refractory period of the first pathway, the refractory period of the second pathway, and the degree of conduction delay (dampening) in the second pathway produced by an early atrial impulse are all functions of the atrial cycle length (time interval 12 in FIG. 2) and the sympathetic-parasympathetic balance of the autonomic nervous system (which is generally reflected in the atrial cycle length), the $A_2$ echo zone will vary with changes in the atrial cycle length. Therefore, the $A_2$ echo zone will be defined for ranges of atrial cycle length 12 (i.e. 300–399 milliseconds, 400–499 milliseconds, 500–649 milliseconds, 650–799 milliseconds, 800–1000 milliseconds, and greater than 1000 milliseconds, or other appropriate interval ranges) for each individual. In accordance with the system of the present invention, it has been found that, if an aborting electrical stimulus $S_{A3}$ is delivered from the pacemaker to the atrial cardiac muscle through the interconnecting electrical conduit within a certain time range with respect to the preceding inciting atrial impulse $A_2$ referred to herein as the "$A_3$ aborting zone", the aborting atrial impulse $A_3$ resulting from the aborting electrical stimulus $S_{A3}$ will function to abort the dual pathway tachycardia which might have occured as a result of the inciting atrial impulse $A_2$ as illustrated schematically in FIG. 3. The aborting electrical stimulus $S_{A3}$ must be delivered to the atrial cardiac muscle at a point in time after the inciting atrial impulse signal $A_2$ has been sensed or detected and at a point in time such that the resulting aborting atrial impulse $A_3$ is received by the initially conducting first or second pathway (the second pathway for example) before the inciting atrial impulse $A_2$ returning towards the atria through the pathway other than the initially conducting pathway (the first pathway for example) has reentered the initially conducting first or second pathway (the second pathway for example), as illustrated in FIGS. 3, 12, and 16. In addition the aborting electrical stimulus $S_{A3}$ must be delivered to the atrial cardiac muscle during the period of time after the sensed inciting atrial impulse signal $A_2$ at which the atrial cardiac cells have been reconditioned to respond to the $S_{A3}$ stimulus by producing an aborting atrial impulse $A_3$ which is conducted to the junction of the first and second pathways near the atria at a time *before* the initially conducting first or second pathway (the second pathway for example) has been reconditioned to conduct the aborting atrial impulse $A_3$ toward the ventricles, the result being: (1) block of the aborting atrial impulse $A_3$ in the initially conducting first or second pathway (the second pathway for example as illustrated in FIGS. 3, 12, and 16 and marked by the reference numeral 24); and (2) penetration of the aborting atrial impulse $A_3$ into the pathway other than the initially conducting first or second pathway (the first pathway for example as illustrated in FIGS. 3, 12, and 16 and marked by the reference numeral 25) such that the inciting atrial impulse $A_2$ returning towards the atria through the pathway other than the initially conducting first or second pathway (the first pathway for example) collides with the aborting atrial impulse $A_3$, extinguishing both impulses as illustrated in FIGS. 3, 12, and 16 and marked by the reference numeral 26. The overall result is failure of conduction of the aborting atrial impulse $A_3$ to the ventricles and failure of the returning inciting atrial impulse $A_2$ to reenter the initially conducting pathway, aborting the initiation of the dual pathway tachycardia.

In accordance with the system of the present invention, the start time and stop time of the $A_3$ aborting zone illustrated in FIG. 3 and designated therein by the reference numerals 27 and 28, respectively, define the limits of the $A_3$ aborting zone and the start time 27 and stop time 28 of the $A_3$ aborting zone are defined with respect to the sensed signal of the inciting atrial impulse $A_2$. The time interval from the sensed inciting atrial impulse signal $A_2$ up to but not including the start time 27 (designated by the reference numeral 30 in FIG. 3) represents the interval of time during which an electrical stimulus delivered from the pacemaker controller to the atrial cardiac cells through the interconnecting electrical conduit will either: (1) fail to elicit an atrial response (atrial depolarization) as the stimulus is delivered within the refractory period of the atrial cardiac cells (period of time following the inciting atrial impulse $A_2$ during which the atrial cardiac cells cannot be reexcited) at the site of the electrical conduit; or (2) the resulting atrial impulse penetrates and blocks in both pathways (due to arriving at the pathways while the conducting cells in those pathways are still refractory following the penetration by the inciting atrial impulse $A_2$) and the conducting time of the inciting atrial impulse $A_2$ through the initially conducting first or second pathway (the second pathway for example) is sufficiently long to allow both pathways to recover excitability following the penetration of those pathways by the atrial impulse induced by the pacemaker electrical stimulus, then the returning inciting atrial impulse $A_2$ can be conducted back towards the atria through the pathway other than the intially conducting first or second pathway (the first pathway for example) and reenter the initially conducting first or second pathway (the second pathway for example) and be conducted towards the ventricles, initiating the dual pathway tachycardia. The stop time 28 of the $A_3$ aborting zone is defined as the time after which an electrical stimulus delivered from the pacemaker controller through the electrical conduit to the atrial cardiac cells will induce an atrial impulse which will either: (1) arrive at the initially conducting first or second pathway (the second pathway for example) after the inciting atrial impulse $A_2$ returning towards the atria through the pathway other than the initially conducting first or second pathway (the first pathway for example) has reentered the initially conducting first or second pathway (the second pathway for example); or (2) arrive at the initially conducting first or second pathway (the second pathway for example) at a time before the inciting atrial impulse $A_2$ returning towards the atria through the pathway other than the initially conducting first or second pathway (the first pathway for example) arrives at the initially conducting first or second pathway (the second pathway for example), but arrives after the initially conducting first or second pathway (the second pathway for example) has been reconditioned to accept and conduct the pacemaker induced atrial impulse towards the ventricles, the result being failure to abort the dual pathway tachycardia. The time interval between the start time 27 and the stop time 28 is defined herein as the $A_3$ aborting zone and is the interval of time during which an electrical stimulus $S_{A3}$ delivered from the pacemaker to the atrial cardiac cells through the interconnecting electrical conduit will induce an aborting atrial impulse $A_3$ which is conducted: (1) to the initially conducting first or second pathway (the second pathway for example) at such a time that the initially conducting first or second pathway (the second pathway for example) has not been reconditioned to receive and conduct the aborting atrial impulse $A_3$ to the ventricles; and (2) into the pathway other than the initially conducting first or second pathway (the first pathway for example), the result being: (1) block of the aborting atrial impulse $A_3$ in the initially conducting first or second pathway (the second pathway for example) as represented schematically and marked by the reference numeral 24 in FIGS. 3, 12, and 16; and (2) conduction of the aborting atrial impulse $A_3$ through the pathway other than the initially conducting first or second pathway (the first pathway for example) towards the ventricles, represented schematically and marked by the reference numeral 25 in FIGS. 3, 12, and 16, which then collides with and extinguishes the inciting atrial impulse $A_2$ returning towards the atria through that pathway represented schematically and marked by the reference numeral 26 in FIGS. 3, 12, and 16, the overall result being the aborting of the dual pathway tachycardia.

For each atrial cycle length there is an ideal definable $A_2$ echo zone and for each atrial cycle length and inciting atrial impulse $A_2$ there is an ideal definable $A_3$ aborting zone. Further, the $A_2$ echo zones and the $A_3$ aborting zones are believed to vary from individual to individual. However as a practical matter and in accordance with the system of the present invention, an $A_2$ echo zone and an $A_3$ aborting zone is determined and defined with respect to predetermined ranges of atrial cycle lengths, and these defined $A_2$ echo zones and $A_3$ aborting zones further are adjusted to accommodate the variances which may occur for different individuals. Thus, according to the system of the present invention, the $A_2$ echo zone and the $A_3$ aborting zone for each of a plurality of ranges of atrial cycle lengths are determined and these determined zones then are massaged to allow for variances in individuals.

Set forth in the Table below are the $A_2$ echo zones and the $A_3$ aborting zones determined for various paced atrial cycle lengths in two patients (individuals) with a dual pathway tachycardia.

TABLE

| PATIENT (Individual) NUMBER | ATRIAL CYCLE LENGTH (Milliseconds) | $A_2$ ECHO ZONE AS MEASURED FROM ATRIAL IMPULSE $A_1$ | | $A_3$ ABORTING ZONE AS MEASURED FROM INCITING ATRIAL IMPULSE $A_2$ LISTED AT LEFT | |
|---|---|---|---|---|---|
| | | START TIME 20 (Milliseconds) | STOP TIME 22 (Milliseconds) | START TIME 27 (Milliseconds) | STOP TIME 28 (Milliseconds) |
| 1 | 500 | 250 | | 150 | 260 |
| | | | 270 | 170 | 260 |
| | 400 | 260 | | 160 | 290 |

TABLE-continued

| PATIENT (Individual) NUMBER | ATRIAL CYCLE LENGTH (Milliseconds) | A₂ ECHO ZONE AS MEASURED FROM ATRIAL IMPULSE A₁ | | A₃ ABORTING ZONE AS MEASURED FROM INCITING ATRIAL IMPULSE A₂ LISTED AT LEFT | |
|---|---|---|---|---|---|
| | | START TIME 20 (Milliseconds) | STOP TIME 22 (Milliseconds) | START TIME 27 (Milliseconds) | STOP TIME 28 (Milliseconds) |
| | | | 270 | 160 | 260 |
| 2 | 600 | 230 | | 150 | 300 |
| | | | 280 | 160 | 270 |
| | 400 | 250 | 250 | 170 | 340 |

From this data, albeit limited, it is evident that the duration of the $A_3$ aborting zone for each atrial cycle length is relatively long in comparison to the duration of the $A_2$ echo zone and that the start time 27 of the $A_3$ aborting zone is at a longer time with respect to the inciting atrial impulse $A_2$ for the inciting atrial impulse $A_2$ at the stop time 22 of the $A_2$ echo zone than for the inciting atrial impulse $A_2$ occurring at the start time 20 of the $A_2$ echo zone because in all of the above instances: (1) the start time 27 of the $A_3$ aborting zone occurred immediately after the atrial cardiac cells at the site of the interconnecting electrical conduit had been reconditioned to respond to the electrical stimulus by producing an atrial impulse, in other words the start time 27 of the $A_3$ aborting zone occurred immediately following the end of the atrial refractory period resulting from the inciting atrial impulse $A_2$; and (2) the atrial refractory period typically prolongs as the atrial impulse $A_2$ occurs later in time with respect to the atrial impulse $A_1$. It is also evident that the $A_3$ aborting zones overlap considerably for the inciting atrial impulse $A_2$ occurring at the start time 20 of the $A_2$ echo zone and for the inciting atrial impulse $A_2$ occurring at the stop time 22 of the $A_2$ echo zone. From a practical standpoint with respect to this invention, for any given range of atrial cycle length, an aborting atrial impulse $A_3$ occurring at an interval of time after the inciting atrial impulse $A_2$ equal to the total of 20 milliseconds plus the interval of the $A_3$ aborting zone start time (marked by the reference numeral 30 in FIG. 3) for an inciting atrial impulse $A_2$ occurring at the stop time 22 of the $A_2$ echo zone, would effectively abort the dual pathway tachycardia for any inciting atrial impulse $A_2$ occurring at the given atrial cycle length. For example, in patient (individual) number one in the table above, if during an atrial cycle length of 500 milliseconds the pacemaker controller delivered an electrical stimulus $S_{A3}$ to induce an aborting atrial impulse $A_3$ at an interval of time following the sensed signal of the inciting atrial impulse $A_2$ equal to 20 milliseconds plus 170 milliseconds or 190 milliseconds, such an aborting atrial impulse $A_3$ would abort the dual pathway tachycardia for any inciting atrial impulse $A_2$ in the $A_2$ echo zone at an atrial cycle length of 500 milliseconds. However, this invention allows the pacemaker controller to deliver an aborting electrical stimulus $S_{A3}$ at a time during the $A_3$ aborting zone.

In some hearts susceptible to a dual pathway tachycardia, such a tachycardia can be induced by an early or premature impulse originating in the ventricles. As shown schematically in FIG. 4, such an inciting ventricular impulse $(V_2)_x$ occurs at a time in which one of the first or second pathways (the first pathway for example) has been reconditioned to accept and conduct the inciting ventricular impulse $(V_2)_x$ towards the atria while the other of the first or second pathways (the second pathway for example) has not been reconditioned (still refractory to excitation) to accept and conduct the inciting ventricular impulse $(V_2)_x$ towards the atria while the other of the first or second pathways (the second pathway for example) has not been reconditioned (still refractory to excitation) to accept and conduct the inciting ventricular impulse $(V_2)_x$ towards the atria, the result being: (1) conduction of the inciting ventricular impulse $(V_2)_x$ towards the atria through the initially conducting first or second pathway (the first pathway for example) as illustrated in FIG. 4 and labeled therein by the reference numeral 32; and (2) block of the inciting ventricular impulse $(V_2)_x$ in the pathway other than the initially conducting first or second pathway (second pathway for example), as illustrated in FIG. 4 and labeled by the reference numeral 32, and if the inciting ventricular impulse $(V_2)_x$ conducted through the initially conducting first or second pathway (first pathway for example) arrives at the junction of the two pathways near the atria at a time in which the pathway other than the initially conducting first or second pathway (second pathway for example) has been reconditioned, that impulse may penetrate and be conducted towards the ventricles through the pathway other than the initially conducting first or second pathway (second pathway for example) as illustrated in FIG. 4 and labeled by the reference numeral 33, producing another ventricular impulse referred to herein and in the art as a ventricular echo impulse $V_e$, and if the impulse conducted towards the ventricles through the pathway other than the initially conducting first or second pathway (second pathway for example) arrives at the junction of the two pathways near the ventricles at a time in which the initially conducting first or second pathway (first pathway for example) has been reconditioned to accept and conduct the impulse, that impulse may reenter the initially conducting first or second pathway (first pathway for example) and be conducted back towards the atria as illustrated in FIG. 4 and marked by the reference numeral 34. The repetitive reentering of the conducted impulse between the two pathways constitutes a dual pathway tachycardia. Thus, there is a period of time between the received ventricular impulse $V_1$ and a time when an inciting ventricular impulse $(V_2)_x$ might occur and this period of time is illustrated diagrammatically and marked by the reference numeral 35 in FIG. 4. The period of time 35 is the longer of the ventricular refractory period (period of time following the last received ventricular impulse $V_1$ during which the ventricles cannot be reexcited) or the period of time following the last received ventricular impulse $V_1$ during which the conducting cells in both the first and second pathways still are refractory to excitation (not yet reconditioned to receive and conduct the ventricular impulse towards the atria) and a ventricular impulse received during this period of time 35 simply will be blocked in both the first and second pathways and will not result in either conduction of the ventricular impulse to the atrial or the initiation of the dual pathway tachycardia. The stop time of this period 35 is designated in FIG. 4 by the reference numeral 36. In addition, there is a time after receipt of a ventricular impulse $V_1$ after which another received ventricular impulse will not constitute an inciting ventricular impulse $(V_2)_x$ because either: (1) the conducting cells in both the first and second pathways are reconditioned (receptive) and a ventricular impulse received within this period of time simply will be conducted towards the atria through both the first and second pathways resulting only in a single atrial impulse; or (2) the ventricular impulse is received sufficiently early in time with respect to the last received ventricular impulse $V_1$ that the conducting cells in one of the first or second pathways (second pathway for example) still are refractory to excitation and the cells in the other pathway (first pathway for example) have been reconditioned to receive and conduct the ventricular impulse towards the atria, but not sufficiently early to either prevent enough penetration of the ventricular impulse into the initially blocking pathway (second pathway for example) or to produce sufficient conduction delay through the initially conducting pathway (first pathway for example) such that when the impulse traveling towards the atria through the initially conducting pathway (first pathway for example) arrives at the junction of the two pathways near the atria and penetrates the initially blocking pathway (the second pathway for example) and attempts to conduct through that pathway back toward the ventricles, that impulse encounters cells which have not yet become reconditioned to accept and conduct the impulse, extinguishing the impulse and preventing the initiation of a dual pathway tachycardia. This time after which an inciting ventricular impulse $(V_2)_x$ will not occur is shown in FIG. 4 and designated therein by the reference numeral 37. The time period between the time 36 and the time 37 is defined herein as the $(V_2)_x$ echo zone. Thus the $(V_2)_x$ echo zone is the time period beginning at a time before which an inciting ventricular impulse $(V_2)_x$ could not occur (time 36) and ending at a time after which an inciting ventricular impulse $(V_2)_x$ could not occur (time 37). An impulse originating in the ventricles within the $(V_2)_x$ echo zone is defined herein as an inciting ventricular impulse $(V_2)_x$ which will result in a dual pathway tachycardia absent some intervention to abort the oncoming dual pathway tachycardia.

The first atrial impulse resulting from conduction of an inciting ventricular impulse $(V_2)_x$ through the initially conducting first or second pathway to the atria is referred to herein as an inciting atrial impulse $(A_2)_x$. The timing of such an inciting atrial impulse $(A_2)_x$ is herein defined with respect to the last sensed atrial impulse signal $A_1$, this interval of time being schematically illustrated and marked by the reference numeral 38 in FIG. 4. However, as it pertains later in the discussion, the timing of such an inciting atrial impulse $(A_2)_x$ could also be defined with respect to the sensed ventricular impulse signal $(V_2)_x$ this interval of time being schematically illustrated in FIG. 4 and marked therein by the reference numeral 94. The earliest and latest times which an inciting atrial impulse $(A_2)_x$ can occur following an inciting ventricular impulse $(V_2)_x$ are represented schematically in FIG. 4 and marked therein by the reference numerals 39 and 40, respectively. The time interval between the times 39 and 40 is herein defined as the $(A_2)_x$ echo zone and the times 39 and 40 are herein defined as the start time and stop time of the $(A_2)_x$ echo zone, respectively. The $(A_2)_x$ echo zone is expected to vary for different ranges of atrial cycle length and from individual to individual. In addition the start time 39 and stop time 40 of the $(A_2)_x$ echo zone may differ from the start time 20 and stop time 22 of the $A_2$ echo zone, respectively, for any given range of atrial cycle lengths, specifically the start time 39 and stop time 40 of the $(A_2)_x$ echo zone may occur at a later time with respect to the last received atrial impulse signal $A_1$ than the start time 20 and stop time 22 of the $A_2$ echo zone, respectively.

An electrical stimulus $S_{(A3)_x}$ delivered from the pacemaker controller to the atrial cardiac cells through the interconnecting electrical conduit and timed from the sensed atrial impulse signal $(A_2)_x$ (the timing interval being illustrated in FIG. 5 and marked therein by the reference numeral 41) will induce an aborting atrial impulse $(A_3)_x$ which is expected to abort the initiation of the dual pathway tachycardia resulting from the inciting ventricular impulse $(V_2)_x$ by a mechanism similar to that of the aborting atrial impulse $A_3$ if that aborting atrial impulse $(A_3)_x$ arrives at the junction of the two pathways near the atria at a time before the arrival of the inciting ventricular impulse $(V_2)_x$ returning toward the atrium through the initially conducting first or second pathway (the first pathway for example and that returning impulse is marked by the reference numeral 34 in FIGS. 4 and 5) and at a time during which the conducting cells of the pathway other than the initially conducting pathway (the second pathway for example) still are refractory to excitation (unreceptive), the result being: (1) the blocking of the aborting atrial impulse $(A_3)_x$ in the pathway other than the initially conducting pathway (the second pathway for example) as illustrated in FIG. 5 and marked therein by the reference numeral 42; and (2) the collison in the initially conducting pathway (the first pathway for example) of the aborting atrial impulse $(A_3)_x$ being conducted towards the ventricles and the inciting ventricular impulse $(V_2)_x$ being conducted towards the atria, extinguishing both impulses as illustrated in FIG. 5 and marked by the reference numeral 43, the overall result being the aborting of the dual pathway tachycardia. Thus, there is a period of time following the sensed inciting atrial impulse signal $(A_2)_x$ illustrated in FIG. 5 and marked by the reference numeral 41, before which an electrical stimulus $S_{(A3)_x}$ delivered from the pacemaker controller to the atrial cardiac cells will not induce an aborting atrial impulse $(A_3)_x$ because either: (1) the atrial cardiac cells still are refractory to excitation (not yet reconditioned) following the received inciting atrial impulse $(A_2)_x$ and therefore the electrical stimulus will not result in an atrial impulse; or (2) the resulting atrial impulse penetrates and blocks in both pathways (due to the arrival of the atrial impulse at the junction of the two pathways near the atria at a time while the conducting cells of both pathways still are refractory to excitation) and the conduction time of the inciting ventricular impulse $(V_2)_x$ returning towards the atria through the initially conducting first or second pathway (the first pathway for example as illustrated in FIG. 5 and marked therein by the reference numeral 34) is sufficiently long to allow the cells of both pathways to recover excitability (become reconditioned) following the penetration of those pathways by the atrial impulse induced by the pacemaker electrical stimulus, then the returning inciting ventricular impulse $(V_2)_x$ can be conducted towards the atria through the initially conducting pathway (the first pathway for example) and reenter the pathway other than the initially conducting pathway (the second pathway for example) and be conducted through that pathway towards the ventricles initiating the dual pathway tachycardia. The stop time of this time interval 41 before which a pacemaker electrical stimulus delivered to the atrial cardiac cells will not induce an aborting atrial impulse $(A_3)_x$ is designated by the reference numeral 44 and illustrated in FIG. 5. There is also a time following the sensed inciting atrial impulse $(A_2)_x$ designated by the reference numeral 45 and illustrated in FIG. 5, after which a pacemaker electrical stimulus delivered to the atrial cardiac cells will not result in an aborting atrial impulse $(A_3)_x$ because the resulting atrial impulse will either: (1) arrive at the junction of the two pathways near the atria at a time after the inciting ventricular impulse $(V_2)_x$ returning towards the atria through the initially conducting pathway (the first pathway for example) has reentered the pathway other than the initially conducting pathway (the second pathway for example) and is being conducted through the latter pathway towards the ventricles; or (2) arrive at the junction of the two pathways near the atria at a time after the conducting cells of the pathway other than the initially conducting pathway (the second pathway for example) have become reconditioned to accept and conduct the atrial impulse towards the ventricles, the result being the failure to abort the dual pathway tachycardia. The time interval between the time 44 and the time 45, during which an electrical stimulus $S_{(A3)x}$ delivered from the pacemaker controller to the atrial cardiac cells will induce an aborting atrial impulse $(A_3)_x$, is herein defined as the $(A_3)_x$ aborting zone and is illustrated in FIG. 5.

For practical purposes as relates to this invention, in individuals in whom the dual pathway tachycardia can be initiated by an inciting ventricular impulse $(V_2)_x$ and cannot be initiated by an inciting atrial impulse $A_2$, the start time 39 and stop time 40 of the $(A_2)_x$ echo zone and the start time 44 and stop time 45 of the $(A_3)_x$ aborting zone can be defined for each of the predetermined ranges of atrial cycle length and these values can be programmed into the system of the present invention to abort the initiation of the dual pathway tachycardia by inciting ventricular impulses $(V_2)_x$'s.

In individuals in whom the dual pathway tachycardia can be initiated by both inciting atrial impulses $A_2$ and inciting ventricular impulse $(V_2)_x$, the start and stop times of the $A_2$ and $(A_2)_x$ echo zones and the start and stop times of the $A_3$ and $(A_3)_x$ aborting zones can be determined for each of the predetermined ranges of atrial cycle length, and in individuals in whom there is a satisfactory degree of overlap between the two echo zones and between the two aborting zones for all ranges of atrial cycle length, the two echo zones for each range of atrial cycle lengths can be combined to form one new and larger echo zone, defined herein as the combined $A_2$-$(A_2)_x$ echo zone and being illustrated in the left panel of FIG. 5A, the start time of which is the smaller of the start times 20 and 39 (time 20 for example) and the stop time of which is the larger of the stop times 22 and 40 (time 40 for example), this combined $A_2$-$(A_2)_x$ echo zone identifying all inciting atrial impulses $A_2$ and every inciting atrial impulse $(A_2)_x$ resulting from all inciting ventricular impulses $(V_2)_x$ for that range of atrial cycle lengths, and the two aborting zones for those ranges of atrial cycle lengths can be combined to form a new single atrial aborting zone, defined herein as the combined $A_3$-$(A_3)_x$ aborting zone and being illustrated in the right panel of FIG. 5A, the start time of which is the larger of the start times 27 and 44 (time 44 for example) and the stop time of which is the smaller of the stop times 28 and 45 (time 45 for example), and during which an electrical stimulus $S_{A3}$-$S_{(A3)x}$ delivered from the pacemaker controller to the atrial cardiac cells through the interconnecting electrical conduit will induce an aborting atrial impulse $A_3$-$(A_3)_x$ which will abort the initiation of the dual pathway tachycardia by an inciting atrial impulse $A_2$ and any inciting ventricular impulse $(V_2)_x$.

However, for individuals in whom there is not sufficient overlap of the $A_3$ and $(A_3)_x$ aborting zones for each range of atrial cycle lengths to determine a single combined atrial aborting zone $A_3$-$(A_3)_x$ for each range of atrial cycle lengths, this invention allows for the use of a second electrical conduit connecting the pacemaker controller to the ventricular cardiac cells for the purpose of sensing signals from ventricular impulses. This invention could be constructed to identify atrial impulses occuring within the $(A_2)_x$ echo zone separately from atrial impulses occuring in the $A_2$ echo zone by determining the number of ventricular impulse signals occuring between the atrial impulse signal in question and the last received atrial impulse signal $A_1$. In other words, the controller would determine whether an atrial impulse occurred within the $A_2$ echo zone only if a single ventricular impulse signal $V_1$ was sensed between the last received atrial impulse signal $A_1$ and the atrial impulse signal in question, and the controller would determine whether an atrial impulse occurred within the $(A_2)_x$ echo zone only if two ventricular impulse signals (the ventricular impulse signal $V_1$ corresponding to the last received atrial impulse signal $A_1$ and the second ventricular impulse signal representing the inciting ventricular impulse signal $(V_2)_x$ were sensed between the last received atrial impulse signal $A_1$ and the atrial impulse signal in question. Further criteria for the $(A_2)_x$ echo zone could be established such that the second ventricular impulse signal must occur at a time interval 35 within the preprogrammed $(V_2)_x$ echo zone with respect to the last received ventricular impulse signal $V_1$ as illustrated schematically in FIG. 4 for the various atrial cycle length ranges and or the received atrial impulse signal $(A_2)_x$ must occur within a specified time interval 94 with respect to the preceding ventricular impulse $(V_2)_x$ for the various ranges of atrial cycle lengths. The separate $A_2$ and $(A_2)_x$ echo zones would then have separate $A_3$ and $(A_3)_x$ aborting zones, respectively, each of which would be defined for each of the predetermined ranges of atrial cycle lengths for that individual.

Alternatively, for individuals in whom the dual pathway tachycardia can be initiated by an inciting ventricular impulse $(V_2)_x$, the system of the present invention, by using two electrical conduits connecting the pacemaker controller with both the atrial cardiac cells and the ventricular cardiac cells, could be modified such that the electrical conduit connecting the pacemaker controller to the ventricular cardiac cells would be used to sense all ventricular impulse signals and determine whether each such ventricular impulse, which follows the last received ventricular impulse $V_1$ without an intervening atrial impulse, occurs within the start time 36 and stop time 37 of the $(V_2)_x$ echo zone as described above and illustrated schematically in FIG. 4, and, on identifying such an inciting ventricular impulse $(V_2)_x$, the pacemaker controller would deliver an electrical stimulus $S_{(A3)y}$ to the atrial cardiac cells through the electrical conduit connecting the pacemaker controller to the atrial cardiac cells which would induce an aborting atrial impulse $(A_3)_y$ which would abort the initiation of the dual pathway tachycardia as illustrated schematically in FIG. 5B. Such an electrical stimulus $S_{(A3)y}$ timed from the sensed inciting ventricular impulse signal $(V_2)_x$ as illustrated schematically in FIG. 5B and marked therein by the reference numeral 46 would induce an aborting atrial impulse $(A_3)_y$ if that impulse arrives at the junction of the two pathways near the atria at a time: (1) before the inciting ventricular impulse $(V_2)_x$ traveling towards the atria through the intially conducting first or second pathway (the first pathway for example) arrives at the junction of the two pathways near the atria; and (2) while the conducting cells of the pathway other than the initially conducting pathway (the second pathway for example) still are refractory to excitation and therefore unable to conduct the aborting atrial impulse $(A_3)_y$ towards the ventricles through that pathway, the result being: (1) block of the aborting atrial impulse $(A_3)_y$ in the pathway other than the initially conducting pathway (the second pathway for example) as illustrated schematically in FIG. 5B and marked therein by the reference numeral 48; and (2) collision in the initially conducting pathway (the first pathway for example) of the aborting atrial $(A_3)_y$ impulse traveling towards the ventricles and the inciting ventricular impulse $(V_2)_x$ traveling towards the atria as illustrated in FIG. 5B and marked therein by the reference numeral 49, the overall result being the aborting of the initiation of the dual pathway tachycardia by the inciting ventricular impulse $(V_2)_x$. Thus, there is a period of time 46 following the sensed inciting ventricular impulse signal $(V_2)_x$ before which a pacemaker electrical stimulus delivered to the atrial cardiac cells will not result in an aborting atrial impulse $(A_3)_y$ because either: (1) the atrial cardiac cells at the site of the atrial electrical conduit still are refractory to excitation (not yet reconditioned) following the last received atrial impulse $A_1$ and therefore the electrical stimulus will not result in an atrial impulse; or (2) the resulting atrial impulse penetrates and blocks in the atrial side of both pathways (due to the arrival of the atrial impulse at the junction of the two pathways near the atria at a time while the conducting cells of both pathways still are refractory to excitation following the last received atrial impulse $A_1$) and the conduction time of the inciting ventricular impulse $(V_2)_x$ traveling towards the atria through the initially conducting pathway (the first pathway for example) is sufficiently long to allow the cells of both pathways to recover excitability (become reconditioned) following the penetration of these pathways by the atrial impulse induced by the pacemaker electrical stimulus, then the inciting ventricular impulse $(V_2)_x$ can be conducted towards the atria through the initially conducting pathway (the first pathway for example) and enter the pathway other than the initially conducting pathway (the second pathway for example) and be conducted through the latter pathway towards the ventricles initiating the dual pathway tachycardia. The stop time of this time interval 46 before which a pacemaker electrical stimulus delivered to the atrial cardiac cells will not induce an aborting atrial stimulus $(A_3)_y$ is designated by the reference numeral 50 and illustrated in FIG. 5B. There is also a time following the sensed inciting ventricular impulse signal $(V_2)_x$, designated by the reference numeral 52 and illustrated in FIG. 5B, after which a pacemaker electrical stimulus delivered to the atrial cardiac cells will not result in an aborting atrial impulse $(A_3)_y$ because the resulting atrial impulse will either: (1) arrive at the junction of the two pathways near the atria at a time after the inciting ventricular impulse $(V_2)_x$ traveling to the atria through the initially conducting pathway (the first pathway for example) has entered the pathway other than the initially conducting pathway (the second pathway for example) and is being conducted through the latter pathway towards the ventricles; or (2) arrive at the junction of the two pathways near the atria at a time after the conducting cells of the pathway other than the initially conducting pathway (the second pathway for example) have become reconditioned to accept and conduct the atrial impulse induced by the pacemaker electrical stimulus towards the ventricles, the result being the failure to abort the dual pathway tachycardia. The time interval between the time 50 and the time 52, during which an electrical stimulus delivered from the pacemaker controller to the atrial cardiac cells will induce an aborting atrial impulse $(A_3)_y$, is herein defined as the $(A_3)_y$ aborting zone and is illustrated in FIG. 5B.

This invention also allows for the use, in at least three ways, of the electrical conduit connecting the pacemaker controller to the ventricular cardiac cells to deliver electrical stimuli to the ventricular cardiac cells for the purpose of inducing a ventricular impulse which would abort the initiation of a dual pathway tachycardia by inciting ventricular impulses $(V_2)_x$ or by inciting atrial impulses $A_2$, and these three methods are illustrated schematically in FIGS. 6, 7, and 8. These methods generally, but not necessarily, would be used in conjunction with an electrical conduit connecting the pacemaker controller to the atrial cardiac cells. In one application not necessarily requiring the use of an additional electrical conduit connecting the pacemaker controller to the atrial cardiac cells, on sensing and identifying an inciting ventricular impulse signal $(V_2)_x$ as described above and illustrated in FIG. 4, the pacemaker controller would deliver an electrical stimulus $S_{(A3)z}$, timed from the sensed inciting ventricular impulse signal $(V_2)_x$ as illustrated in FIG. 6 and marked by the reference numeral 54, which would induce an aborting ventricular impulse $(V_3)_z$ which is conducted to the junction of the two pathways near the ventricles at such a time: (1) before the inciting ventricular impulse $(V_2)_x$ returning towards the ventricles through the pathway other than the initially conducting pathway (the second pathway for example) arrives at the junction of the two pathways near the ventricles; and (2) while the conducting cells of the initially conducting pathway (the first pathway for example) still are refractory to excitation following the received inciting ventricular impulse $(V_2)_x$ and are therefore unable to conduct the aborting ventricular impulse $(V_3)_z$ towards the atria through that pathway, the result being: (1) block of the aborting ventricular impulse $(V_3)_z$ in the initially conducting pathway (the first pathway for example) as illustrated schematically in FIG. 6 and represented therein by the reference numeral 56; and (2) collision in the pathway other than the initially conducting pathway (the second pathway for example) of the aborting ventricular impulse $(V_3)_z$ traveling towards the atria and the inciting ventricular impulse $(V_2)_x$ traveling back towards the ventricles as illustrated in FIG. 6 and marked therein by the reference numeral 58, the overall result being the aborting of the initiation of the dual pathway tachycardia by the inciting ventricular impulse $(V_2)_x$. Thus, there is a period of time 54 following the sensed ventricular impulse signal $(V_2)_x$ before which a pacemaker electrical stimulus delivered to the ventricular cardiac cells through the electrical conduit connecting the pacemaker controller to the ventricular cardiac cells will not result in an aborting ventricular impulse $(V_3)_z$ because either: (1) the ventricular cardiac cells at the site of the electrical conduit still are refractory to excitation (not yet reconditioned following the received inciting ventricular impulse $(V_2)_x$), and therefore the electrical stimulus will not result in a ventricular impulse; or (2) the resulting ventricular impulse penetrates and blocks in the ventricular side of both pathways [due to the arrival of the ventricular impulse at the junction of the two pathways near the ventricles at a time while the conducting cells of both pathways still are refractory to excitation following the received inciting ventricular impulse $(V_2)_x$] and the conduction time of the inciting ventricular impulse $(V_2)_x$ returning towards the ventricles through the pathway other than the initially conducting pathway (the second pathway for example) is sufficiently long to allow the cells of both pathways to recover excitability (become reconditioned) following the penetration of those pathways by the ventricular impulse induced by the pacemaker electrical stimulus, then the inciting ventricular impulse $(V_2)_x$ can be conducted to the ventricles through the pathway other than the initially conducting pathway (the second pathway for example) and be conducted through the latter pathway back towards the atria initiating the dual pathway tachycardia. The stop time of this interval 54 before which a pacemaker electrical stimulus delivered to the ventricular cardiac cells will not induce an aborting ventricular impulse $(V_3)_z$ is designated by the reference numeral 60 and illustrated in FIG. 6. There is also a time following the sensed inciting ventricular impulse signal $(V_2)_x$ after which a pacemaker electrical stimulus delivered to the ventricular cardiac cells will not result in an aborting ventricular impulse $(V_3)_z$ because the resulting ventricular impulse will either: (1) arrive at the junction of the two pathways near the ventricles at a time when the inciting ventricular impulse $(V_2)_x$ traveling back toward the ventricles through the pathway other than the initially conducting pathway (the second pathway) has already reentered the initially conducting pathway (the first pathway for example) and is being conducted through the latter pathway back towards the atria; or (2) arrive at the junction of the two pathways near the ventricles at a time after the conducting cells of the initially conducting pathway (the first pathway for example) have become reconditioned to accept and conduct the ventricular impulse induced by the pacemaker electrical stimulus towards the atria, the result being the failure to abort the dual pathway tachycardia. The time interval after which a pacemaker electrical stimulus delivered to the ventricular cardiac cells following the second ventricular impulse signal $(V_2)_x$ will not result in an aborting ventricular impulse $(V_3)_z$ is designated by the reference numeral 62 and illustrated in FIG. 6. The time interval between the time 60 and the time 62, during which an electrical stimulus delivered from the pacemaker controller to the ventricular cardiac cells will induce an aborting ventricular impulse $(V_3)_z$, is herein defined as the $(V_3)_z$ aborting zone as illustrated in FIG. 6.

In a second application requiring the use of two electrical conduits connecting the pacemaker controller with both the atrial and the ventricular cardiac cells, on sensing an inciting atrial impulse signal $A_2$ and a corresponding inciting ventricular impulse signal $V_2$, the pacemaker controller would deliver an aborting electrical stimulus $S_{V_3}$ to the ventricular cardiac cells through the interconnecting electrical conduit to induce an aborting ventricular impulse $V_3$ for the purpose of aborting the dual pathway tachycardia. An inciting ventricular impulse $V_2$ is herein defined as the ventricular impulse resulting from conduction to the ventricles through the initially conducting pathway (the second pathway for example) of an inciting atrial impulse $A_2$, the inciting atrial impulse $A_2$ being defined above and illustrated schematically in FIG. 2. An inciting ventricular impulse signal $V_2$ is further defined for each of the predetermined ranges of atrial cycle lengths as: (1) the first ventricular impulse occuring after a sensed inciting atrial impulse signal $A_2$; and (2) occurs within a range of intervals 64 with respect to the received inciting atrial impulse signal $A_2$ as illustrated schematically in FIG. 7, and that range of intervals 64 is herein defined as the $V_2$ echo zone, the start and stop times of which are designated by the reference numerals 66 and 68, respectively and illustrated in FIG. 7. The start time 66 of the $V_2$ echo zone is the time interval 64 before which any inciting atrial impulse $A_2$ for a given range of atrial cycle lengths will not be associated with the initiation of a dual pathway tachycardia and the stop time 68 is the time interval 64 after which any inciting atrial impulse $A_2$ for a given range of atrial cycle lengths will not be associated with the initiation of a dual pathway tachycardia. Therefore the time interval between the start time 66 and the stop time 68, known as the $V_2$ echo zone is the full range of intervals 64 (the time interval 64 being the time interval between a sensed inciting atrial impulse $A_2$ and the first ventricular impulse signal resulting from that inciting atrial impulse $A_2$) for which any inciting atrial impulse $A_2$ will be associated for the initiation of a dual pathway tachycardia to occur, the start time 60 and stop time 62 of the $V_2$ echo zone being expected to vary with changes in atrial cycle length just as the start time 20 and stop time 22 of the $A_2$ echo zone is expected to vary with changes in the atrial cycle length. On sensing an inciting atrial impulse signal $A_2$ and a corresponding inciting ventricular impulse signal $V_2$, the pacemaker controller would deliver an aborting electrical stimulus $S_{V_3}$, timed from the sensed inciting ventricular impulse signal $V_2$ as illustrated in FIG. 7 and marked by the reference numeral 70, which would induce an aborting ventricular impulse $V_3$ which is conducted to the junction of the two pathways near the ventricles at such a time: (1) before the inciting atrial impulse $A_2$ returning towards the ventricles through the initially conducting pathway (the second pathway for example) arrives at the junction of the two pathways near the ventricles; and (2) while the conducting cells in the pathway other than the initially conducting pathway (the first pathway for example) still are refractory to excitation and therefore unable to conduct the aborting ventricular impulse $V_3$ towards the atria through that pathway, the result being: (1) block of the aborting ventricular impulse $V_3$ in the pathway other than the initially conducting pathway (the first pathway for example) as illustrated schematically in FIG. 7 and marked therein by the reference numeral 72; and (2) collision in the initially conducting pathway (the second pathway for example) of the aborting ventricular impulse $V_3$ traveling towards the atria and the inciting atrial impulse $A_2$ traveling back towards the ventricles as illustrated in FIG. 7 and marked therein by the reference numeral 74, the overall result being the aborting of the initiation of the dual pathway tachycardia by the inciting atrial impulse $A_2$. Thus, there is a period of time 70 following the sensed inciting ventricular impulse signal $V_2$ before which a pacemaker electrical stimulus, delivered to ventricular cardiac cells through the electrical conduit connecting the pacemaker controller to the ventricular cardiac cells, will not result in an aborting ventricular impulse $V_3$ because either: (1) the ventricular cardiac cells at the site of electrical conduits still are refractory to excitation (not yet reconditioned following the received inciting ventricular impulse $V_2$), and therefore the electrical stimulus will not result in a ventricular impulse; or (2) the resulting ventricular impulse penetrates and blocks in the ventricular side of both pathways (due to the arrival of the ventricular impulse at the junction of the two pathways near the ventricles at a time while the conducting cells of both pathways still a refractory to excitation) and the conduction time of the inciting atrial impulse $A_2$ returning towards the ventricles through the initially conducting pathway (the second pathway for example) is sufficiently long to allow the cells of both pathways to recover excitability (become reconditioned) following the penetration of those pathways by the ventricular impulse induced by the pacemaker stimulus, then the inciting atrial impulse $A_2$ can be conducted to the ventricles through the initially conducting pathway (the second pathway for example) and reenter the pathway other than the initially conducting pathway (the first pathway for example) and be conducted through the latter pathway towards the atria initiating the dual pathway tachycardia. The stop time of this interval 70 before which a pacemaker electrical stimulus delivered to ventricular cardiac cells will not induce an aborting ventricular impulse $V_3$ is designated by the reference numeral 76 and illustrated in FIG. 7. There is also a time following the sensed inciting ventricular impulse $V_2$, designated by the reference numeral 78 and illustrated in FIG. 7, after which a pacemaker electrical stimulus delivered to the ventricular cardiac cells will not result in an aborting ventricular impulse $V_3$ because the resulting ventricular impulse will either: (1) arrive at the junction of the two pathways near the ventricles at a time after the inciting atrial impulse $A_2$ returning towards the ventricles through the initially conducting pathway (the second pathway for example) has reentered the pathway other than the initially conducting pathway (the first pathway for example) and is being conducted through the latter pathway towards the atria; or (2) arrive at the junction of the two pathways near the ventricles at a time after the conducting cells of the pathway other than the initially conducting pathway (the first pathway for example) have become reconditioned to accept and conduct the ventricular impulse towards the atria, the result being the failure to abort the dual pathway tachycardia. The time interval between the time 76 and the time 78, during which an electrical stimulus $S_{V_3}$ delivered from the pacemaker controller to the ventricular cardiac cells will induce an aborting ventricular impulse $V_3$ is herein defined as the $V_3$ aborting zone and is illustrated in FIG. 7.

In a third application, also requiring the use of two electrical conduits connecting the pacemaker controller with both the atrial and ventricular cardiac cells, on sensing an inciting atrial impulse signal $A_2$ as described above and illustrated schematically in FIG. 2, the pacemaker controller would deliver an electrical stimulus $S_{(V_3)R}$ timed from the sensed inciting atrial impulse signal $A_2$ as illustrated in FIG. 8 and marked therein by the reference numeral 80, which would induce an aborting ventricular impulse $(V_3)_R$ which is conducted to the junction of the two pathways near the ventricles at a time: (1) before the inciting atrial impulse $A_2$ traveling towards the ventricles through the initially conducting pathway (the second pathway for example) arrives at the junction of the two pathways near the ventricles; and (2) while the conducting cells of the pathway other than the initially conducting pathway (the first pathway for example) still are refractory to excitation and therefore cannot conduct the aborting ventricular impulse $(V_3)_R$ towards the atria through that pathway, the result being: (1) block of the aborting ventricular impulse $(V_3)_R$ in the pathway other than the initially conducting pathway (the first pathway for example) as illustrated schematically in FIG. 8 and represented by the reference numeral 82; and (2) collision in the initially conducting pathway (the second pathway for example) of the aborting ventricular impulse $(V_3)_R$ traveling towards the atria and the inciting atrial impulse $A_2$ traveling towrds the ventricles as illustrated schematically in FIG. 8 and marked by the reference numeral 84, the overall result being the aborting of the initiation of the dual pathway tachycardia by the inciting atrial impulse $A_2$. Thus, there is a period of time 80 before which a pacemaker electrical stimulus delivered to the ventricular cardiac cells through the electrical conduit connecting the pacemaker controller to the ventricular cardiac cells will not result in an aborting ventricular impulse $(V_3)_R$ because either: (1) the ventricular cardiac cells at the site of the electrical conduit still are refractory to excitation (not yet reconditioned following the last received ventricular impulse $V_1$) and therefore the electrical stimulus will not result in a ventricular impulse; or (2) the resulting ventricular impulse penetrates and blocks in the ventricular side of both pathways (due to the arrival of the ventricular impulse at the junction of the two pathways near the ventricles at a time while the conducting cells of both pathways still are refractory to excitation following the last received atrial impulse $A_1$) and the conduction time of the inciting atrial impulse $A_2$ traveling towards the ventricles through the initially conducting pathway (the second pathway for example) is sufficiently long to allow the cells of both pathways to recover excitability (become reconditioned) following the penetration of those pathways by the ventricular impulse induced by the pacemaker electrical stimulus, then the inciting atrial impulse can be conducted to the ventricles through the initially conducting pathway (the second pathway for example) and enter the pathway other than the initially conducting pathway (the first pathway for example) and be conducted through the latter pathway towards the atria initiating the dual pathway tachycardia. The start time of this interval 80 before which a pacemaker electrical stimulus delivered to the ventricular cardiac cells will not induce an aborting ventricular impulse $(V_3)_R$ is illustrated in FIG. 8 and designated therein by the reference numeral 86. There is also a period of time following the sensed inciting atrial impulse signal $A_2$, illustrated schematically in FIG. 8 and designated therein by the reference numeral 88, after which a pacemaker electrical stimulus delivered to the ventricular cardiac cells will not result in an aborting ventricular impulse $(V_3)_R$ because the resulting ventricular impulse will either: (1) arrive at the junction of the two pathways near the ventricles at a time after the inciting atrial impulse $A_2$ traveling towards the ventricles through the initially conducting pathway (the second pathway for example) has already entered the pathway other than the initially conducting pathway (the first pathway for example) and is being conducted through the latter pathway back towards the atria; or (2) arrive at the junction of the two pathways near the ventricles at a time after the conducting cells in the pathway other than the initially conducting pathway (the first pathway for example) have become reconditioned to accept and conduct the ventricular impulse induced by the pacemaker electrical stimulus towards the atria, the result being the failure to abort the dual pathway tachycardia. The time interval between the time 86 and the time 88, during which an electrical stimulus $S_{(V3)R}$ delivered from the pacemaker controller to the ventricular cardiac cells will induce an aborting ventricular impulse $(V_3)_R$, is herein defined as the $(V_3)_R$ aborting zone and is illustrated in FIG. 8.

The present system contemplates utilizing conventional, commercially available pacemakers or, at least, pacemakers which are constructed to function in a manner like conventional, commercially available pacemakers, and it is contemplated that either or both circuitry and programming of the controller of such conventional pacemakers is modified to incorporate the system of the present invention. Such pacemakers are commercially available from such companies as Cordis Corporation of Miami, Fla., for example, and thus a detailed description of the function or construction of such commercially available pacemakers is not deemed necessary.

In accordance with the system of the present invention, a pacemaker having a controller and an electrical conduit which is attached to the atrial cardiac muscle and/or an electrical conduit which is attached to the ventricular cardiac muscle is installed in an individual. A description of the use of such a device with a single electrical conduit attached to the atrial cardiac cells is as follows. The controller of the pacemaker is adapted to sense atrial impulse signals $A_1$'s and continuously to average and update the atrial cycle lengths for a predetermined number of atrial impulses prior to each of received atrial impulses $A_1$'s. An averaging number of atrial impulses in the range of from about four to twelve atrial impulses is believed to be adequate.

The last determined average atrial cycle length continuously is stored in the controller memory. In addition, the predetermined $A_2$ echo zone and/or $(A_2)_x$ echo zone or the combined $A_2$-$(A_2)_x$ echo zone and the predetermined $A_3$ aborting zone and/or $(A_3)_x$ aborting zone or the combined $A_3$-$(A_3)_x$ aborting zone for the various ranges of atrial cycle lengths also are stored in the controller memory.

When the controller receives a sensed atrial impulse signal, the controller first determines the period of time lapsed between the received atrial impulse signal and the last received atrial impulse signal $A_1$ thereby establishing the position of the received atrial impulse signal with respect to the last received atrial impulse signal $A_1$. Then, the controller determines the $A_2$ echo zone and/or $(A_2)_x$ echo zone or the combined $A_2$-$(A_2)_x$ echo zone for the last determined average atrial cycle length (the last determined atrial cycle length falls within a predetermined preset range of atrial cycle lengths and for this range of atrial cycle lengths the controller has programmed therein the predetermined echo zone(s) and this is the echo zone(s) determined in this last mentioned step by the controller). The time period between the received atrial impulse signal and the last received atrial impulse signal $A_1$ then is compared to the determined $A_2$ echo zone and/or $(A_2)_x$ echo zone or the combined $A_2$-$(A_2)_x$ echo zone and the controller functions to establish whether or not the time of the received atrial impulse signal falls within the determined echo zone(s). If the time of the received atrial impulse signal is not within the determined echo zone(s), the received atrial impulse signal is determined to be an atrial impulse $A_1$ and not to be an atrial inciting impulse $A_2$ and the controller, in this instance, does not function to deliver an aborting electrical stimulus to the atrial cardiac muscle. If the time of the received atrial impulse signal is determined to be within the determined $A_2$, $(A_2)_x$, or combined $A_2$-$(A_2)_x$ echo zone, the received atrial impulse signal is determined to be an inciting atrial impulse $A_2$ or $(A_2)_x$, and the controller then determines the $A_3$, $(A_3)_x$, or combined $A_3$-$(A_3)_x$ aborting zone, respectively, for the last determined average atrial cycle length in a manner just like that described before with respect to the determination of the echo zone(s) [the echo zone(s) and the aborting zone(s) could be determined at the same time in this sequence of steps if desired in a particular application]. When the controller determines that an inciting atrial impulse $A_2$ or $(A_2)_x$ has been received, the controller then functions to deliver an aborting electrical stimulus $S_{(A3)x}$ or combined $S_{A3}$-$S_{(A3)x}$ at a time within the respective predetermined aborting zone established for the last determined average atrial cycle length and this aborting electrical stimulus is conducted to the atrial cardiac muscle by way of the electrical conduit connecting the controller to the atrial cardiac muscle thereby inducing the aborting atrial impulse $A_3$, $(A_3)_x$, or the combined $A_3$-$(A_3)_x$.

Preferably, the controller is programmed to deliver the aborting electrical stimulus at a time within the respective aborting zone as near as practically possible to the start time of that aborting zone for the particular average atrial cycle length. The delivery of the aborting electrical stimulus at this particular time is believed to provide the safest assurance that the resulting aborting atrial impulse in fact will be delivered in time to abort the onset of the dual pathway tachycardia which otherwise would result from the sensed or detected inciting atrial impulse $A_2$ or $(A_2)_x$.

As mentioned before, the electrical conduit from the controller in a pacemaker can be attached to virtually any part of the endocardial (inside) surface of the right atrial wall, the endothelial (inside) surface of the coronary sinus, or to the epicardial (outside) surface of the right or left atrium, but is normally is attached to endocardial (inside) surface of the the right atrium at a position in the right atrial appendage near the sinoatrial node or, at least, in the upper portion of the right atrium (see FIG. 1). In the system of the present invention, it is important to sense or detect an inciting atrial impulse $A_2$ or $(A_2)_x$ and to deliver the aborting electrical stimulus $A_3$ or $(A_3)_x$ at a location as close as possible to the atrial side of the first or second pathway which conducts the inciting impulse $A_2$ or $(V_2)_x$ towards the ventricles (the second pathway for example as illustrated in FIGS. 2 and 4 and marked therein by the reference numerals 90 and 33, respectively) to allow the earliest possible start time of the $A_3$ and $(A_3)_x$ aborting zones with respect to the last received atrial impulse $A_1$ and increase the likelihood that the resulting aborting atrial impulse $A_3$ or $(A_3)_x$ will arrive at the atrial side of that pathway before the arrival of the inciting impulse $A_2$ or $(V_2)_x$ returning towards the atria over the other pathway (the first pathway for example being illustrated in FIGS. 3 and 5 and marked therein by the reference numerals 92 and 34, respectively) and while the conducting cells of the former pathway (the second pathway for example) still are refractory to excitation and therefore unable to conduct the aborting atrial impulse $A_3$ or $(A_3)_x$ towards the ventricles. In general, the farther the site of atrial sensing is from the atrial side of the first or second pathway which conducts the inciting impulse $A_2$ or $(V_2)_x$ towards the ventricles (the second pathway for example), the longer will be the atrial conduction time of the inciting atrial impulse $A_2$ or $(A_2)_x$ to the site of atrial sensing therefore falsely prolonging the time interval 18 or 35, respectively, between the last sensed atrial impulse signal $A_1$ and the sensed inciting atrial impulse signal $A_2$ or $(A_2)_x$. In addition, since the start times 27 and 44 of the $A_3$ and $(A_3)_x$ aborting zones, respectively, are both expected to occur just after the atrial cardiac cells at the site of the electrical conduit recover excitability (the end of the refractory period) following the inciting atrial impulse $A_2$ or $(A_2)_x$, and since the duration of the refractory period of the atrial cardiac cells following the inciting atrial impulse $A_2$ or $(A_2)_x$ lengthens as the interval 18 or 38 lengthens, the false lengthening of the inverval 18 or 38 will further delay the start time 27 or 44 of the $A_3$ or $(A_3)_x$ aborting zone, respectively. Also, since the aborting atrial impulse $A_3$ or $(A_3)_x$ must be conducted to the atrial side of the first or second pathway which conducts the inciting impulse $A_2$ or $(V_2)_x$ towards the ventricles (the second pathway for example) before producing its effect on aborting the initiation of the dual pathway tachycardia, the farther the site of delivery to the atrial cardiac cells of the aborting electrical stimulus $S_{A3}$ or $S_{(A3)_x}$ from the atrial side of that pathway, the longer will be the atrial conduction time to the atrial side of that pathway of the aborting atrial impulse $A_3$ or $(A_3)_x$, respectively, having the effect of further delaying the start time 27 or 44 of the $A_3$ or $(A_3)_x$ aborting zone, respectively, and decreasing the likelihood that the aborting atrial impulse $A_3$ or $(A_3)_x$ will, in fact, reach the atrial side of that pathway in time to abort the initiation of the dual pathway tachycardia. In general, the first or second pathway which conducts the inciting impulse $A_2$ or $(V_2)_x$ towards the ventricles (the second pathway for example) will be located in the atrioventricular node for both forms of dual pathway tachycardia. Thus, in accordance with the system of the present invention, the electrical conduit can be attached to virtually any part of the atrial cardiac muscle but it is desirable to attach the electrical conduit to a position in the atrial cardiac muscle as close as possible to the atrioventricular node.

The system of the present invention can also be applied with a single electrical conduit connecting the pacemaker controller to the ventricular cardiac muscle in a manner similar to that described above. In this instance, the controller of the pacemaker is adapted to sense ventricular impulse signals and continuously to average and update the ventricular cycle lengths for a predetermined number of ventricular impulses. The last determined average ventricular cycle length continuously is stored in the controller memory. In addition, the $(V_2)_x$ echo zone and $(V_3)_z$ aborting zone for the various ranges of ventricular cycle lengths also are stored in the controller memory. When the controller receives a ventricular impulse signal, the controller determines the period of time between the received ventricular impulse signal and the last received ventricular impulse signal $V_1$, thereby establishing the position of the received ventricular impulse signal with respect to the last received ventricular impulse signal $V_1$. Then, the controller determines the $(V_2)_x$ echo zone for the range of ventricular cycle lengths in which the last determined average ventricular cycle length occurs. The time period between the received ventricular impulse signal and the last received ventricular impulse signal $V_1$ then is compared to the determined $(V_2)_x$ echo zone and the controller functions to establish whether or not the time of the received ventricular impulse falls within the determined $(V_2)_x$ echo zone. If the time of the received ventricular impulse signal is not within the $(V_2)_x$ echo zone the received ventricular impulse signal is determined to be a ventricular impulse $V_1$ and not to be an inciting ventricular impulse $(V_2)_x$, and the controller, in this instance, does not function to deliver an aborting electrical stimulus to the ventricular cardiac muscle. If the time of the received ventricular impulse signal is determined to be within the $(V_2)_x$ echo zone, the received ventricular impulse signal is determined to be an inciting ventricular impulse $(V_2)_x$, and the controller then determines the $(V_3)_z$ aborting zone for the last determined average ventricular cycle length and delivers an aborting electrical stimulus $S_{(V3)_z}$ to the ventricular cardiac muscle through the interconnecting electrical conduit. For this application, it is desirable that the electrical conduit be attached to the ventricular cardiac muscle in a location as close as possible to the ventricular side of the first or second pathway which conducts the inciting ventricular impulse $(V_2)_x$ towards the atria (the first pathway for example as illustrated schematically in FIG. 6) for the same reason as described in the paragraph above for positioning the atrial electrical conduits as close as possible to the first or second pathway which conducts the inciting impulse $A_2$ or $(V_2)_x$ towards the ventricles. In the condition of atrioventricular nodal reentry, that position would be as near as possible to the ventricular side of the atrioventricular node, while in the condition at atrioventricular reentry using an accessory A-V pathway for retrograde conduction that position would be as near as possible to the ventricular side of the accessory A-V pathway (or anomalous A-V connection, see FIG. 1).

The system of the present invention can also be applied with two electrical conduits, one connecting the pacemaker controller to the atrial cardiac muscle and the other connecting the pacemaker controller to the ventricular cardiac muscle. In this instance, the controller of the pacemaker is adapted to sense both atrial impulse signals and ventricular impulse signals and continuously to average and update the atrial cycle lengths for a predetermined number of atrial impulses. The last determined average atrial cycle length continuously is stored in the controller memory. In addition the $A_2$, $(V_2)_x$, $V_2$ and/or $(A_2)_x$ echo zones and the $A_3$, $(A_3)_x$, $(A_3)_y$, $(V_3)_z$, $V_3$ and/or $(V_3)_R$ aborting zones for the various ranges of ventricular cycle lengths also are stored in the controller memory. Such a system could determine whether each received atrial impulse signal following the last received atrial impulse $A_1$ with only a single intervening ventricular impulse signal $V_1$ represents an inciting atrial impulse $A_2$ by criteria limited to the interval of time between the received atrial impulse and the last received atrial impulse $A_1$ and the last average atrial cycle length (simple $A_2$ echo zone criteria) or could require the additional criteria that the received atrial impulse be followed by a ventricular impulse signal $V_2$ occuring within a specific interval of time 64 with respect to the received atrial impulse signal (i.e. occuring within the $V_2$ echo zone as illustrated in FIG. 7). Similarly, such a system could determine whether each received ventricular impulse signal following the last received ventricular impulse signal $V_1$ without an intervening atrial impulse signal represents an inciting ventricular impulse $(V_2)_x$ by criteria limited to the interval of time between the received ventricular impulse signal and the last received ventricular impulse signal $V_1$ and the last average atrial cycle length (simple $(V_2)_x$ echo zone criteria), or could require the additional criterion that the received ventricular impulse signal be followed by an atrial impulse signal occuring within a specific interval of time 94 from the received ventricular impulse signal or within a specific interval of time 38 from the last received atrial impulse signal $A_1$ (i.e. occuring within the $(A_2)_x$ echo zone as illustrated in FIG. 4). On identifying an atrial impulse signal as representing an inciting atrial impulse $A_2$, the pacemaker controller could be programmed to either: (1) deliver an aborting electrical stimulus $S_{A3}$, timed from the inciting atrial impulse signal $A_2$ and during the $A_3$ aborting zone for the last average atrial cycle length to the atrial cardiac cells through the electrical conduit connecting the pacemaker controller to the atrial cardiac muscle as illustrated schematically in FIG. 3; (2) deliver an aborting electrical stimulus $S_{V3}$, timed from the inciting ventricular impulse signal $V_2$ and during the $V_3$ aborting zone for the last average atrial cycle length, to the ventricular cardiac cells through the electrical conduit connecting the pacemaker controller to the ventricular cardiac muscle as illustrated in FIG. 7; or (3) deliver an aborting electrical stimulus $S_{(V3)R}$, timed from the inciting atrial impulse signal $A_2$ and during the $(V_3)_R$ aborting zone for the last average atrial cycle length to the ventricular cardiac cells through the electrical conduit connecting the pacemaker controller to the ventricular cardiac muscles illustrated in FIG. 8. On identifying a ventricular impulse signal as representing an inciting ventricular impulse $(V_2)_x$, the pacemaker controller could be programmed to either: (1) deliver an aborting electrical stimulus $S_{(A3)x}$, timed from the inciting atrial impulse signal $(A_2)_x$ and during the $(A_3)_x$ aborting zone for the last average atrial cycle length to the atrial cardiac cells through the electrical conduit connecting the pacemaker controller to the atrial cardiac muscle as illustrated in FIG. 5; (2) deliver an aborting electrical stimulus $S_{(A3)y}$, timed from the inciting ventricular impulse signal $(V_2)_x$ and during the $(A_3)_y$ aborting zone for the last average atrial cycle length, to the atrial cardiac cells through the electrical conduit connecting the pacemaker controller to the atrial cardiac muscle as illustrated schematically in FIG. 5B; or (3) deliver an aborting electrical stimulus $S_{(A3)z}$ timed from the inciting ventricular impulse $(V_2)_x$ and during the $(V_3)_z$ aborting zone for the last average atrial cycle length, to the ventricular cardiac cells through the electrical conduit connecting the pacemaker controller to the ventricular cardiac muscle as illustrated schematically in FIG. 6. The preferred locations for attachment of the atrial and ventricular electrical conduits are the same as described in the two paragraphs above.

Changes may be made in the incorporation of the system of the present invention in pacemakers and changes may be made in the step or the sequence of steps of the system of the present invention without departing from the spirit and scope of the present invention as defined in the following claims.

What is claimed is:

1. A system for aborting the initiation of a dual pathway tachycardia in a heart producing cardiac impulses induced as a result of an inciting cardiac impulse, comprising the steps of:
   determining at least one time range, each time range being an echo zone, following a cardiac impulse within which an inciting cardiac impulse may occur resulting in a dual pathway tachycardia;
   determining at least one time range, each time range being an aborting zone, following an inciting cardiac impulse within which an aborting cardiac impulse may be induced in the cardiac muscle for aborting the dual pathway tachycardia which otherwise would have occurred as a result of the inciting cardiac impulse;
   sensing cardiac impulses in a heart;
   determining a sensed inciting cardiac impulse as a sensed cardiac impulse sensed at a time within the echo zone; and
   inducing an aborting cardiac impulse at a time within the aborting zone in response to sensing an inciting cardiac impulse.

2. The system of claim 1 wherein the heart's cardiac impulses have cardiac cycle lengths (the time between maximum amplitudes of adjacent cardiac impulses, the cardiac cycles occurring in varying lengths which are referred to as ranges of cardiac cycle lengths); and wherein the step of determining at least one echo zone is defined further to include determining a plurality of echo zones, each echo zone being determined for each of a plurality of predetermined ranges of cardiac cycle lengths; and wherein the step of determining at least one aborting zone is defined further to include determining a plurality of aborting zones, each aborting zone being determined for each of a plurality of the predetermined ranges of cardiac cycle lengths; and wherein the step of sensing the cardiac impulses is defined further to include the period of time lapsed between the sensed cardiac impulse and the last sensed cardiac impulse; and wherein the system is defined further to include the steps of:
   continuously determining the cardiac cycle length;
   continuously determining an average cardiac cycle length for a predetermined time period or a predetermined number of sensed cardiac impulses prior to the last sensed cardiac impulse;
   determining the lapse of time between each sensed cardiac impulse and the last sensed cardiac impulse;
   determining, for each sensed cardiac impulse, the echo zone and the aborting zone corresponding to the last determined average cardiac cycle length; and
   comparing the determined lapse of time between each sensed cardiac impulse and the last sensed cardiac impulse with the echo zone determined from the last determined average cardiac cycle length to determine if the sensed cardiac impulse occurred at a time within such determined echo zone thereby determining if the sensed cardiac impulse is an inciting cardiac impulse; and wherein the step of inducing the aborting cardiac impulse is defined further as delivering an aborting electrical stimulus to the cardiac muscle at a time within the aborting zone determined from the last determined average cardiac cycle length to induce aborting cardiac impulse.

3. The system of claim 2 wherein the aborting zone has a start time and a stop time, and wherein the step of inducing the aborting cardiac impulse is defined further as inducing the aborting cardiac impulse at a time within the aborting zone determined from the last determined average cardiac cycle length and at a time relatively close in time to the start time of the aborting zone.

4. The system of claim 2 wherein the echo zone is defined further as having a start time spaced in time a predetermined time period from the last sensed cardiac impulse signal and a stop time spaced in time a predetermined time period from the last sensed cardiac impulse signal.

5. The system of claim 4 wherein the aborting zone is defined further to include a start time and a stop time, the start time of the aborting zone being spaced in time a predetermined time period from the inciting cardiac impulse and the stop time of the aborting zone being spaced a predetermined time period from the inciting cardiac impulse.

6. The system of claim 5 wherein the heart includes a first pathway for conducting an electrical impulse generally between the atria and the ventricles and a second pathway for conducting an electrical impulse generally between the atria and the ventricles, the first and second pathway each having conducting cells which will function to conduct an electrical impulse when reconditioned (including repolarization) and which require a period of time after being depolarized to be reconditioned for conducting a subsequently received electrical impulse and the period of time for reconditioning after being depolarized is referred to as the refractory period, and wherein the start time of the echo zone is defined further as being a time after the last sensed cardiac impulse signal when the conducting cells in one of the first and second pathways are reconditioned and the conducting cells in the other one of the first and second pathways are not yet reconditioned.

7. The system of claim 6 wherein the echo zone is defined further as being a period of time after a last sensed cardiac impulse during which an inciting cardiac impulse conducted through one of the first and second pathways can be conducted back through the other one of the first and second pathways to produce a cardiac echo impulse, the conducting cells in the last mentioned other one of the first and second pathways being reconditioned for conducting such a returning impulse.

8. The system of claim 1 wherein the dual pathway tachycardia is defined further as being due to atrioventricular nodal reentry wherein the atrioventricular node in the heart includes a first pathway adapted for conducting an electrical impulse generally between the atria and the ventricles and a second pathway adapted for conducting an electrical impulse generally between the atria and the ventricles; and wherein the step of determining the echo zone is defined further as determining the $A_2$ echo zone following a sensed atrial impulse $A_1$ within which an inciting atrial impulse $A_2$ may occur resulting in dual pathway tachycardia; and wherein the step of determining the aborting zone is defined further as determining the $A_3$ aborting zone following an inciting atrial impulse $A_2$ within which an aborting atrial impulse $A_3$ may be induced in the atria for aborting the dual pathway tachycardia which otherwise would have occurred as a result of the inciting atrial impulse $A_2$; and wherein the step of sensing cardiac impulses is defined further as sensing atrial impulses $A_1$'s in a heart (an inciting atrial impulse $A_2$ being an atrial impulse $A_1$ which occurs at a time within the $A_2$ echo zone) and wherein the step of inducing an aborting cardiac impulse is defined further as inducing an aborting atrial impulse $A_3$ at a time within the $A_3$ aborting zone in response to sensing an inciting atrial impulse $A_2$.

9. The system of claim 8 wherein the heart's cardiac impulses have cardiac cycle lengths (the time between maximum amplitudes of adjacent cardiac impulses, the cardiac cycles occurring in varying lengths which are referred to as ranges of cardiac cycle lengths); and wherein the step of determining at least one echo zone is defined further to include determining an $A_2$ echo zone for each of a plurality of predetermined ranges of atrial cycle lengths; and wherein the step of determining at least one aborting zone is defined further to include determining an $A_3$ aborting zone for each of a plurality of the predetermined ranges of atrial cycle lengths; and wherein the step of sensing the atrial impulses $A_1$'s is defined further as determining the period of time lapsed between the sensed atrial impulse $A_1$ and the last sensed atrial impulse $A_1$; and wherein the system is defined further to include the steps of:

continouously determining the atrial cycle length;

continuously determining an average atrial cycle length for a predetermined time period or a predetermined number of sensed atrial impulses $A_1$'s prior to the last sensed atrial impulse;

determining the lapse of time between each sensed atrial impulse $A_1$ and the last sensed atrial impulse $A_1$;

determining, for each sensed atrial impulse $A_1$, the $A_2$ echo zone and the $A_3$ aborting zone corresponding to the last determined average atrial cycle length; and comparing the determined lapse of time between each sensed atrial impulse $A_1$ and the last sensed atrial impulse $A_1$ with the $A_2$ echo zone determined from the last determined average atrial cycle length to determine if the sensed atrial impulse $A_1$ occurred at a time within such determined $A_2$ echo zone thereby determining if the sensed atrial impulse $A_1$ is an inciting atrial impulse $A_2$; and wherein the step of inducing the aborting atrial impulse $A_3$ is defined further as delivering an aborting electrical stimulus $S_{A3}$ to the atrial cardiac muscle at a time within the $A_3$ aborting zone determined from the last determined average atrial cycle length.

10. The system of claim 9 wherein the $A_3$ aborting zone includes a start time and a stop time, and wherein the step of inducing the aborting atrial impulse $A_3$ is defined further as inducing the aborting atrial impulse $A_3$ at a time within the $A_3$ aborting zone determined from the last determined average atrial cycle length and at a time relatively close in time to the start time of the $A_3$ aborting zone.

11. The system of claim 9 wherein the steps of sensing the artial impulses $A_1$'s and inducing the atrial aborting impulse $A_3$ are defined further as sensing the atrial impulses $A_1$ and delivering an aborting electrical stimulus $S_{A3}$ at a position on the atrial cardiac muscle generally near the atrioventricular node to: (1) allow the system to define accurately whether a sensed atrial impulse $A_1$ occurs in the $A_2$ echo zone since the ability of an inciting atrial impulse $A_2$ to induce the form of dual pathway tachycardia referred to as atrioventricular nodal reentry, is in general dependent on the time of the arrival of the inciting atrial impulse $A_2$ at the atrioventricular node rather than the time of the arrival of the inciting atrial impulse $A_2$ elsewhere in the atrial cardiac muscle; and (2) allow the aborting atrial impulse $A_3$ to be induced and conducted to the atrioventricular node in sufficient time to effectively abort the initiation of the dual pathway tachycardia.

12. The system of claim 8 wherein the $A_2$ echo zone is defined further as having a start time spaced in time a predetermined time period from the last sensed atrial impulse $A_1$ and a stop time spaced in time a predetermined time period from the last sensed atrial impulse $A_1$, for each of the predetermined ranges of average atrial cycle length.

13. The system of claim 12 wherein the $A_3$ aborting zone is defined further to include a start time and a stop time, the start time of the $A_3$ aborting zone being spaced in time a predetermined time period from the sensed inciting atrial impulse $A_2$ and the stop time of the $A_3$ aborting zone being spaced a predetermined time period from the sensed inciting atrial impulse $A_2$.

14. The system of claim 13 wherein an inciting atrial impulse $A_2$ is defined further as a atrial impulse received at the atrioventricular node under the following conditions: (1) when the conducting cells in one of the first and second pathways are excitable (receptive); (2) when the conducting cells in the other of the first and second pathways are still refractory (unreceptive) and block any received impulse; (3) when the initially refractory conducting cells in the first or second pathway will be reconditioned (become excitable) in time to receive and conduct the impulse arriving at the junction of the first and second pathways near the ventricles, as a result of conduction of the inciting atrial impulse $A_2$ towards the ventricles through the initially conducting first or second pathway, back towards the atria to produce an atrial echo impulse $A_e$; and (4) when the conducting cells in the initially conducting first or second pathway will be reconditioned in time to receive and conduct the impulse arriving at the junction of the first and second pathways near the atria, as a result of conduction of the impulse towards the atria over the initially refractory first or second pathway, back towards the ventricles, forming a repetitive circuit.

15. The system of claim 14 wherein there is a period of time between a received atrial impulse $A_1$ and a time when an inciting atrial impulse $A_2$ might occur (start time of the $A_2$ echo zone) and this period of time is defined (among other factors) as being the longer of the atrial refractory period (period of time following the prior atrial impulse $A_1$ during which the atria cannot be reexcited) and the period of time following the last sensed atrial impulse $A_1$ during which the conducting cells in both the first and the second pathways still are refractory (not yet reconditioned to receive and conduct the atrial impulse) and an atrial impulse received during this period of time will be blocked in both first and second pathways.

16. The system of claim 15 wherein there is a time (the stop time of the $A_2$ echo zone) after the sensing of an atrial impulse $A_1$ after which another received atrial impulse $A_1$ will not constitute an inciting atrial impulse $A_2$ because (among other factors) either: (1) the conducting cells in both the first and second pathways are reconditioned (receptive) and an atrial impulse received within this period of time will be conducted towards the ventricles through both the first and second pathways; or (2) the atrial impulse $A_1$ is received sufficiently early in time with respect to the preceding atrial impulse $A_1$ that the cells in the first pathway still are refractory to excitation and the cells in the second pathway have recovered excitability (been reconditioned) allowing conduction to the ventricles only through the second pathway, but not sufficiently early to produce the degree of conduction delay in the second pathway (dampening effect) necessary to allow the cells in the first pathway to recover excitability to allow the impulse initially conducted through the second pathway to be conducted back towards the atria through the first pathway.

17. The system of claim 1 wherein the dual pathway tachycardia is defined further as being due to the presence of an anomalous atrioventricular connection wherein the heart includes an anomalous strand of conductive cells which extend around or through the annulus fibrosa to form a first pathway adapted for conducting an electrical impulse generally between the atria and the ventricles and the atrioventricular node provides a second pathway adapted for conducting an electrical impulse generally between the atria and the ventricles; and wherein the step of determining the echo zone is defined further as determining the $A_2$ echo zone following a sensed atrial impulse $A_1$ within which an inciting atrial impulse $A_2$ may occur resulting in dual pathway tachycardia; and wherein the step of determining the aborting zone is defined further as determining the $A_3$ aborting zone following an inciting atrial impulse $A_2$ within which an aborting atrial impulse $A_3$ may be induced in the atria for aborting the dual pathway tachycardia which otherwise would have occurred as a result of the inciting atrial impulse $A_2$; and wherein the step of sensing cardiac impulses is defined further as sensing atrial impulses $A_1$'s in a heart (an inciting atrial impulse $A_2$ being an atrial impulse $A_1$ which occurs at a time in the $A_2$ echo zone); and wherein the step of inducing an aborting cardiac impulse is defined further as inducing an aborting atrial impulse $A_3$ at a time within the $A_3$ aborting zone in response to sensing an inciting atrial impulse $A_2$.

18. The system of claim 17 wherein the heart's cardiac impulses have cardiac cycle lengths (the time between maximum amplitudes of adjacent cardiac impulses, the cardiac cycles occurring in varying lengths which are referred to as ranges of cardiac cycle lengths); and wherein the step of determining at least one echo zone is defined further to include determining an $A_2$ echo zone for each of a plurality of predetermined ranges of atrial cycle lengths; and wherein the step of determining at least one aborting zone is defined further to include determining an $A_3$ aborting zone for each of a plurality of the predetermined ranges of atrial cycle lengths; and wherein the step of sensing the atrial impulses $A_1$'s is defined further as determining the period to time lapsed between the sensed atrial impulse $A_1$ and the last sensed atrial impulse $A_1$; and wherein the system is defined further to include the steps of:

continuously determining the atrial cycle length;

continuously determining an average atrial cycle length for a predetermined time period or a predetermined number of sensed atrial impulses $A_1$'s prior to the last sensed atrial impulse $A_1$;

determining the lapse of time between each sensed atrial impulse $A_1$ and the last sensed atrial impulse $A_1$;

determining, for each sensed atrial impulse $A_1$, the $A_2$ echo zone and the $A_3$ aborting zone corresponding to the last determined average atrial cycle length; and comparing the determined lapse of time between each sensed atrial impulse $A_1$ and the last sensed atrial impulse $A_1$ with the $A_2$ echo zone determined from the last determined average atrial cycle length to determine if the sensed atrial impulse $A_1$ occurred at a time within such determined $A_2$ echo zone thereby determining if the sensed atrial impulse $A_1$ is an inciting atrial impulse $A_2$; and wherein the step of inducing the aborting atrial impulse $A_3$ is defined further as delivering an aborting electrical stimulus $S_{A3}$ to the atrial cardiac muscle at a time within the $A_3$ aborting zone determined from the last determined average atrial cycle length.

19. The system of claim 18 wherein the steps of sensing the atrial impulses $A_1$'s and inducing the atrial aborting impulse $A_3$ are defined further as sensing the atrial impulses $A_1$'s and delivering the aborting electrical stimuli $S_{A3}$'s at a position on the atrial cardiac muscle generally near the atrioventricular node (second pathway), and when practical between the atrioventricular node and the atrial insertion site of the anomalous atrioventricular connection (first pathway) to: (1) allow the system to define accurately whether an atrial impulse $A_1$ occurs within the $A_2$ echo zone because the ability of an atrial impulse $A_1$ to induce the form of dual pathway tachycardia referred to as atrioventricular nodal reentry using an anomalous atrioventricular connection for retrograde conduction is in general dependent on the time of its arrival at the first and second pathways; and (2) allow the aborting atrial impulse $A_3$ to be induced and conducted to the second pathway (atrioventricular node) in sufficient time to effectively abort the initiation of the dual pathway tachycardia.

20. The system of claim 17 wherein the $A_3$ aborting zone includes a start time and stop time, and wherein the step of inducing the aborting atrial impulse $A_3$ is defined further as inducing the aborting atrial impulse $A_3$ at a time within the $A_3$ aborting zone determined from the last determined average atrial cycle length and at a time relatively close in time to the start time of the $A_3$ aborting zone.

21. The system of claim 17 wherein the $A_2$ echo zone is defined further as having a start time spaced in time a predetermined time period from the last sensed atrial impulse $A_1$ and a stop time spaced in time a predetermined time period from the last sensed atrial impulse $A_1$.

22. The system of claim 21 wherein the $A_3$ aborting zone is defined further to include a start time and a stop time, the start time of the $A_3$ aborting zone being spaced in time a predetermined time period from the sensed inciting atrial impulse $A_2$ and the stop time of the $A_3$ aborting zone being spaced a predetermined time period from the sensed inciting atrial impulse $A_2$.

23. The system of claim 17 wherein an inciting atrial impulse $A_2$ is received at the first and second pathways under the following conditions: (1) when the conducting cells in one of the first and second pathways are excitable (receptive); (2) when the conducting cells in the other one of the first and second pathways are still refractory (unreceptive); (3) when the initially refractory conducting cells in the first or second pathway will be reconditioned (become excitable) in time to receive and conduct the impulse arriving at the junction of the first and second pathways near the ventricles, as a result of conduction of the inciting atrial impulse $A_2$ through the initially conducting first or second pathway, back to the atria to produce an atrial echo impulse $A_e$; and (4) when the conducting cells in the initially conducting first or second pathway will be reconditioned in time to receive and conduct the atrial echo impulse $A_e$ back to the ventricles forming a repetitive circuit.

24. The system of claim 23 wherein there is a period of time between a received atrial impulse signal $A_1$ and a time when an inciting atrial impulse $A_2$ might occur (start time of the $A_2$ echo zone) and this period of time is defined as being the longer of the atrial refractory period (period of time following the prior atrial impulse $A_1$ during which the atria cannot be reexcited) and the period of time following the last sensed atrial impulse $A_1$ during which the conducting cells in both the first and the second pathways still are refractory (not yet reconditioned to receive and conduct the atrial impulse) and an atrial impulse received during this period of time will be blocked in both first and second pathways.

25. The system of claim 24 wherein there is a time (the stop time of the $A_2$ echo zone) after the sensing of an atrial impulse signal $A_1$ after which another sensed atrial impulse $A_1$ will not constitute an inciting atrial impulse $A_2$ because either: (1) the conducting cells in both the first and second pathways are reconditioned (receptive) and an atrial impulse $A_1$ received within this period of time will be conducted towards the ventricles through both the first and second pathways; or (2) the atrial impulse $A_1$ is received sufficiently early in time with respect to the preceding atrial impulse $A_1$ that the cells in the first pathway still are refractory to excitation and the cells in the second pathway have recovered excitability (been reconditioned) allowing conduction to the ventricles only through the second pathway, but not sufficiently early to produce the degree of conduction delay in the second pathway (dampening effect) necessary to allow the cells in the first pathway to recover excitability to allow the impulse initially conducted through the second pathway to be conducted back towards the atria through the first pathway.

26. The system of claim 17 wherein the accessory (anomalous) pathway (the first pathway) is defined further as being capable of conduction only in the retrograde direction (from the ventricles to the atria) and wherein an inciting atrial impulse $A_2$ is defined further as being an atrial impulse $A_1$ which occurs at a time after the conducting cells in the second pathway (atrioventricular node) have been reconditioned to conduct an impulse and at a time such that, when the inciting atrial impulse $A_2$ is conducted through the second pathway to the junction of the first and second pathways near the ventricles, the conducting cells in the first pathway have been reconditioned to receive and conduct this impulse back towards the atria thereby producing an atrial echo impulse $A_e$ and at such a time so that, when the atrial echo impulse $A_e$ is received by the conducting cells in the second pathway, the conducting cells in the second pathway have had sufficient time to be reconditioned for receiving and conducting this atrial echo impulse $A_e$ back towards the ventricles initiating a condition of sustained reentering of the second pathway in the antegrade direction (atria to ventricles) and the first pathway in the retrograde direction (ventricles to atria).

27. The system of claim 1 wherein the dual pathway tachycardia is defined as being induced by an inciting ventricular impulse $(V_2)_x$ originating in the ventricles and resulting in an inciting atrial impulse $(A_2)_x$, and wherein the heart includes a first pathway adapted for conducting an electrical impulse generally between the atria and the ventricles and a second pathway adapted for conducting an electrical impulse generally between the atria and the ventricles; and wherein the step of determining the echo zone is defined further as determining the $(A_2)_x$ echo zone following a sensed atrial impulse $A_1$ within which an inciting atrial impulse $(A_2)_x$ may occur as a result of conduction of the inciting ventricular impulse $(V_2)_x$ to the atria through the initially conducting first or second pathway and which result in dual pathway tachycardia; and wherein the step of determining the aborting zone is defined further as determining the $(A_3)_x$ aborting zone following a sensed inciting atrial impulse $(A_2)_x$ within which an aborting atrial impulse $(A_3)_x$ may be induced in the atrial cardiac muscle for aborting the dual pathway tachycardia which otherwise would have occurred as a result of the inciting ventricular impulse $(V_2)_x$ and the subsequent inciting atrial impulse $(A_2)_x$; and wherein the step of sensing cardiac impulses is defined further as sensing atrial impulses $A_1$'s in a heart; and wherein the step of inducing an aborting cardiac impulse is defined further as inducing an aborting atrial impulse $(A_3)_x$ at a time within the $(A_3)_x$ aborting zone in response to sensing an inciting atrial impulse $(A_2)_x$.

28. The system of claim 27 wherein the inciting ventricular impulse $(V_2)_x$ is defined further as occuring at a time in which one of the first or second pathways has been reconditioned to accept and conduct the inciting ventricular impulse $(V_2)_x$ towards the atria while the other one of the first and second pathways has not been reconditioned (still refractory to excitation) to accept and conduct the inciting ventricular impulse $(V_2)_x$ towards the atria, thereby resulting in: (1) conduction of the inciting ventricular impulse $(V_2)_x$ towards the atria through the initially conducting first or second pathway; and (2) block of the inciting ventricular impulse $(V_2)_x$ in the pathway other than the initially conducting first or second pathway, and the inciting ventricular impulse $(V_2)_x$ being further defined as being conducted through the initially conducting first or second pathway and arriving at the junction of the first and second pathways near the atria at a time in which the pathway other than the initially conducting first or second pathway has been reconditioned, that impulse being conducted towards the ventricles through the pathway other than the initially conducting first or second pathway producing another ventricular impulse (ventricular echo impulse $V_e$), and the reconduction of the ventricular echo impulse $V_e$ back toward the atria resulting in a repetitive reentering of the conducted impulse between the first and second pathways (dual pathway tachycardia).

29. The system of claim 28 wherein the inciting ventricular impulse $(V_2)_x$ is defined further as being a ventricular impulse $V_1$ occuring within a $(V_2)_x$ echo zone having a start time and a stop time, the period of time between the last ventricular impulse $V_1$ and a time when an inciting ventricular impulse $(V_2)_x$ might occur being the start time of the $(V_2)_x$ echo zone, this period of time being the longer of the ventricular refractory period (period of time following the last ventricular impulse $V_1$ during which the ventricles cannot be reexcited) and the period of time following the last ventricular impulse $V_1$ during which the conducting cells in both the first and second pathways still are refractory to excitation (not yet reconditioned to receive and conduct the ventricular impulse towards the atria) and a ventricular impulse $V_1$ received during this period of time being blocked in both the first and second pathways.

30. The system of claim 29 wherein the stop time of the $(V_2)_x$ echo zone is defined as being a time after a ventricular impulse $V_1$ after which another received ventricular impulse $V_1$ will not constitute an inciting ventricular impulse $(V_2)_x$ because either: (1) the conducting cells of both the first and second pathways are reconditioned (receptive) and a ventricular impulse received within this period of time simply will be conducted towards the atria through both the first and second pathways resulting only in a single atrial impulse; or (2) the ventricular impulse is received sufficiently early in time with respect to the last received ventricular impulse $V_1$ that the conducting cells in one of the first or second pathways still are refractory to excitation and the cells in the other first or second pathway have been reconditioned to receive and conduct the ventricular impulse towards the atria, but not sufficiently early to either prevent enough penetration of the ventricular impulse into the initially blocking first or second pathway or to produce sufficient conduction delay through the initially conducting first or second pathway such that when the impulse traveling toward the atria through the initially conducting first or second pathway penetrates the initially blocking first or second pathway and attempts to conduct through that pathway back toward the ventricles, that impulse encounters cells which have not yet become reconditioned to accept and conduct the impulse, extinguishing the impulse and preventing the initiation of a dual pathway tachycardia.

31. The system of claim 27 wherein the $(A_2)_x$ echo zone is defined further as having a start time and a stop time, the start time of the $(A_2)_x$ echo zone being the earliest time when an inciting atrial impulse $(A_2)_x$ can occur following an inciting ventricular impulse $(V_2)_x$ and the stop time of the $(A_2)_x$ echo zone being the latest time when an inciting atrial impulse $(A_2)_x$ can occur following an inciting ventricular impulse $(V_2)_x$.

32. The system of claim 31 wherein the heart's cardiac impulses have cardiac cycle lengths (the time between maximum amplitudes of adjacent cardiac impulses, the cardiac cycles occurring in varying lengths which are referred to as ranges of cardiac cycle lengths); and wherein the step of determining at least one echo zone is defined further to include determining an $(A_2)_x$ echo zone for each of a plurality of predetermined ranges of atrial cycle lengths; and determining an $(A_3)_x$ aborting zone for each of a plurality of the predetermined ranges of atrial cycle lengths; and wherein the step of sensing the atrial impulses $A_1$'s is defined further as determining the period of time lapsed between the sensed atrial impulse $A_1$ and the last sensed atrial impulse signal $A_1$; and wherein the system is defined further to include the steps of:

continuously determining the atrial cycle length;
continuously determining an average atrial cycle length for a predetermined time period or a predetermined number of sensed atrial impulses $A_1$'s prior to the last sensed atrial impulse signal $A_1$;

determining the lapse of time between each sensed atrial impulse $A_1$ and the last sensed atrial impulse signal $A_1$;

determining, for each sensed atrial impulse $A_1$, the $(A_2)_x$ echo zone and the $(A_3)_x$ aborting zone corresponding to the last determined average atrial cycle length; and comparing the determined lapse of time between each sensed atrial impulse $A_1$ and the last sensed atrial impulse $A_1$ with the $(A_2)_x$ echo zone determined from the last determined average atrial cycle length to determine if the sensed atrial impulse $A_1$ occurred at a time within such determined $(A_2)_x$ echo zone thereby determining if the sensed atrial impulse $A_1$ is an inciting atrial impulse $(A_2)_x$; and wherein the step of inducing the aborting atrial impulse $(A_3)_x$ is defined further as delivering an aborting electrical stimulus $S_{(A_3)_x}$ to the atrial cardiac muscle at a time within the $(A_3)_x$ aborting zone determined from the last determined average atrial cycle length.

33. The system of claim 32 wherein the step of inducing the aborting atrial impulse $(A_3)_x$ is defined further as inducing the aborting atrial impulse $(A_3)_x$ at a time within the $(A_3)_x$ aborting zone determined from the last determined average atrial cycle length and at a time relatively close in time to the start time of the $(A_3)_x$ aborting zone.

34. The system of claim 31 wherein the step of inducing the aborting atrial impulse $(A_3)_x$ is defined further as delivering an aborting electrical stimulus $S_{(A_3)_x}$ to the atrial cardiac muscle at a time within the $(A_3)_x$ aborting zone to produce the aborting atrial impulse $(A_3)_x$, the aborting atrial impulse $(A_3)_x$ being an atrial impulse arriving at the first or second pathways before the arrival of the inciting ventricular impulse $(V_2)_x$ returning toward the atrium through the initially conducting first or second pathway and at a time during which the conducting cells of the first or second pathway other than the initially conducting first or second pathway still are refractory to excitation (unreceptive), thereby resulting in: (1) the blocking of the aborting atrial impulse $(A_3)_x$ in the first or second pathway other than the initially conducting first or second pathway; and (2) the collison in the initially conducting first or second pathway of the aborting atrial impulse $(A_3)_x$ being conducted towards the ventricles and the inciting ventricular impulse $(V_2)_x$ being conducted back toward the atria, extinguishing both impulses $(A_3)_x$ and $(V_2)_x$ and aborting of the dual pathway tachycardia.

35. The system of claim 34 wherein the $(A_3)_x$ aborting zone is defined further as having a start time and a stop time, the start time of the $(A_3)_x$ aborting zone being a time before which a delivered electrical stimulus $S_{(A_3)_x}$ will not induce an aborting atrial impulse $(A_3)_x$ because either: (1) the atrial cardiac cells still are refractory to excitation (not yet reconditioned) following the received inciting atrial impulse $(A_2)_x$ and the electrical stimulus $S_{(A_3)_x}$ will not result in an atrial impulse; or (2) the resulting atrial impulse penetrates and blocks in both pathways and the conduction time of the inciting ventricular impulse $(V_2)_x$ returning toward the atria through the initially conducting first or second pathway is sufficiently long to allow the cells of both the first and second pathways to recover excitability (become reconditioned) following the penetration of the first and second pathways by the atrial impulse $(A_3)_x$ induced by the electrical stimulus $S_{(A_3)_x}$, then the returning inciting ventricular impulse $(V_2)_x$ can be conducted toward the ventricles through the initially conducting first or second pathway and reenter the first or second pathway other than the initially conducting first or second pathway and be conducted back through that pathway toward the ventricles initiating the dual pathway tachycardia; and the stop time of the $(A_3)_x$ aborting zone being a time after a sensed inciting atrial impulse $(A_2)_x$ after which an electrical stimulus $S_{(A_3)_x}$ delivered to the atrial cardiac muscle will not result in an aborting atrial impulse $(A_3)_x$ because the resulting atrial impulse will either: (1) arrive at the junction of the first and second pathways near the atria at a time after the inciting ventricular impulse $(V_2)_x$ returning towards the atria through the initially conducting first or second pathway has reentered the first or second pathway other than the initially conducting first or second pathway and is being conducted through the first or second pathway other than the initially conducting first or second pathway toward the ventricles; or (2) arrive at the junction of the first and second pathways near the atria at a time after the conducting cells of the first or second pathway other than the initially conducting first or second pathway have become reconditioned to accept and conduct the arial impulse toward the ventricles.

36. The system of claim 1 wherein the dual pathway tachycardia is defined further as being due to either one or both atrioventricular nodal reentry and atrioventricular reentry using an anomalous atrioventricular connection for retrograde and an inciting ventricular impulse $(V_2)_x$ originating in the ventricles and resulting in an inciting atrial impulse $(A_2)_x$ and wherein the heart includes a first pathway adapted for conducting an electrical impulse generally between the atria and the ventricles and a second pathway adapted for conducting an electrical impulse generally between the atria and the ventricles; and wherein the step of determining the echo zone is defined further as determining the $A_2$ echo zone following a sensed atrial impulse $A_1$ within which an inciting atrial impulse $A_2$ may occur resulting in dual pathway tachycardia and determining an $(A_2)_x$ echo zone following a sensed atrial impulse $A_1$ within which an inciting atrial impulse $(A_2)_x$ may occur resulting in dual pathway tachycardia; and wherein the step of determining the aborting zone is defined further as determining the $A_3$ aborting zone following an inciting atrial impulse $A_2$ within which an aborting atrial impulse $A_3$ may be induced in the atrial cardiac muscle for aborting the dual pathway tachycardia which otherwise would have occurred as a result of the inciting atrial impulse $A_2$ and determining the $(A_3)_x$ aborting zone following an inciting atrial impulse $(A_2)_x$ within which an aborting atrial impulse $(A_3)_x$ may be induced in the atrial cardiac muscle for aborting the dual pathway tachycardia which otherwise would have occured as a result of the inciting ventricular impulse $(V_2)_x$ and its resultant inciting atrial impulse $(A_2)_x$; and wherein the step of sensing cardiac impulses is defined further as sensing atrial impulses $A_1$'s in a heart; and wherein the step of inducing an aborting cardiac impulse is defined further as inducing an aborting atrial impulse $A_3$ at a time within the $A_3$ aborting zone in response to sensing an inciting atrial impulse $A_2$ and inducing an aborting atrial impulse $(A_3)_x$ at a time within the $(A_3)_x$ aborting zone in response to sensing an inciting atrial impulse $(A_2)_x$.

37. The system of claim 36 wherein the $A_2$ echo zone has a start time and a stop time and wherein the $(A_2)_x$ echo zone has a start time and a stop time, and wherein the $A_3$ aborting zone has a start time and a stop time, and wherein the $(A_3)_x$ aborting zone has a start time and a stop time and wherein the system is defined further to include: determining the overlapping time period between the $A_2$ echo zone and the $(A_2)_x$ echo zone, the overlapping time period being the combined $A_2$-$(A_2)_x$ echo zone; determining the time period common to both the $A_3$ aborting zone and the $(A_3)_x$ aborting zone, the common time period being the combined $A_3$-$(A_3)_x$ aborting zone; and wherein the step of inducing an aborting cardiac impulse is defined further to include delivering an electrical stimulus $S_{A3}$-$S_{(A3)x}$ to the atrial cardiac muscle to induce an aborting atrial impulse $A_3$-$(A_3)_x$ in response to sensing an inciting atrial impulse $A_2$ and in response to sensing an inciting atrial impulse $(A_2)_x$; and wherein the $A_2$-$(A_2)_x$ echo zone is defined further to have a start time and a stop time, the start time of the $A_2$-$(A_2)_x$ echo zone being the shorter of the start times of the $A_2$ echo zone and the $(A_2)_x$ echo zone and the stop time of the $A_2$-$(A_2)_x$ echo zone being the longer of the stop times of the $A_2$ echo zone and the $(A_2)_x$ echo zone; and wherein the $A_3$-$(A_3)_x$ aborting zone has a start time and a stop time, the start time of the $A_3$-$(A_3)_x$ aborting zone being the longer of the start times of the $A_3$ aborting zone and the $(A_3)_x$ aborting zone and the stop time of the $A_3$-$(A_3)_x$ aborting zone being the shorter of the stop times of the $A_3$ aborting zone and the $(A_3)_x$ aborting zone.

38. The system of claim 37 wherein the heart's cardiac impulses have cardiac cycle lengths (the time between maximum amplitudes of adjacent cardiac impulses, the cardiac cycles occurring in varying lengths which are referred to as ranges of cardiac cycle lengths); and wherein the step of determining at least one echo zone is defined further to include determining a combined $A_2$-$(A_2)_x$ echo zone for each of a plurality of predetermined ranges of atrial cycle lengths; and wherein the step of determining at least one aborting zone is defined further to include determining a combined $A_3$-$(A_3)_x$ aborting zone for each of a plurality of the predetermined ranges of atrial cycle lengths; and wherein the step of sensing the atrial impulses $A_1$'s is defined further as determining the period of time lapsed between the sensed atrial impulse $A_1$ and the last sensed atrial impulse $A_1$; and wherein the system is defined further to include the steps of:

continuously determining the atrial cycle length;
continuously determining an average atrial cycle length for a predetermined time period or a predetermined number of sensed atrial impulses $A_1$'s prior to the last sensed atrial impulse $A_1$;
determining the lapse of time between each sensed atrial impulse $A_1$ and the last sensed atrial impulse $A_1$;
determining, for each received atrial impulse $A_1$, the combined $A_2$-$(A_2)_x$ echo zone and the combined $A_3$-$(A_3)_x$ aborting zone corresponding to the last determined average atrial cycle length; and
comparing the determined lapse of time between each sensed atrial impulse $A_1$ and the last sensed atrial impulse $A_1$ with the combined $A_2$-$(A_2)_x$ echo zone determined from the last determined average atrial cycle length to determine if the received atrial impulse $A_1$ occurred at a time within such determined combined $A_2$-$(A_2)_x$ echo zone thereby determining if the received atrial impulse $A_1$ is an inciting atrial impulse $A_2$-$(A_2)_x$.

39. The system of claim 36 defined further to include: sensing ventricular impulses $V_1$'s; and wherein determining a sensed atrial impulse $A_1$ to be an inciting atrial impulse $A_2$ if such sensed atrial impulse $A_1$ occurred within the $A_2$ echo zone and only a single ventricular impulse $V_1$ was sensed between the last sensed atrial impulse $A_1$ and the sensed atrial impulse $A_1$, and determining an atrial impulse $A_1$ to be an atrial inciting impulse $(A_2)_x$ if such sensed atrial impulse $A_1$ occurred within the $(A_2)_x$ echo zone and only two ventricular impulses $V_1$'s were sensed between the last sensed atrial impulse $A_1$ and the sensed atrial impulse $A_1$ and the second of the two sensed ventricular impulses $V_1$'s occurs at a time following the first of the two sensed ventricular impulses $V_1$'s determined to be within the $(V_2)_x$ echo zone (for the last determined average atrial cycle length), an inciting ventricular impulse $(V_2)_x$ being a ventricular impulse $V_1$ which occurs at a time within the $(V_2)_x$ echo zone.

40. The system of claim 1 wherein the dual pathway tachycardia is defined further as being induced by an inciting ventricular impulse $(V_2)_x$ originating in the ventricles; and wherein the heart includes a first pathway adapted for conducting an electrical impulse generally between the atria and the ventricles and a second pathway adapted for conducting an electrical impulse generally between the atria and the ventricles; and wherein the step of determining the echo zone is defined further as determining the $(V_2)_x$ echo zone within which an inciting ventricular impulse $(V_2)_x$ may occur resulting in dual pathway tacardia; and wherein the step of determining the aborting zone is defined further as determining the $(A_3)_y$ aborting zone within which an aborting atrial impulse $(A_3)_y$ may be induced in the atrial cardiac muscle for aborting the dual pathway tachycardia which otherwise would have occurred as a result of the inciting ventricular impulse $(V_2)_x$; and wherein the step of sensing cardiac impulses is defined further as sensing atrial impulses $A_1$'s and sensing ventricular impulses $V_1$'s in a heart; and wherein the step of inducing an aborting cardiac impulse is defined further as inducing an aborting atrial impulse $(A_3)_y$ at a time within the $(A_3)_y$ aborting zone in response to sensing an inciting ventricular impulse $(V_2)_x$, the inciting ventricular impulse signal $(V_2)_x$ being determined to be a sensed ventricular impulse $V_1$ occuring within the $(V_2)_x$ echo zone without an intervening sensed atrial impulse $A_1$ between the received ventricular impulse $V_1$ and the last sensed atrial impulse signal $A_1$.

41. The system of claim 40 defined further to include delivering an electrical stimulus $S_{(A3)y}$ to the atrial cardiac muscle to induce the aborting impulse $(A_3)_y$.

42. The system of claim 40 wherein the $(A_3)_y$ aborting zone is defined further as having a start time and a stop time, the start time being timed from the sensed inciting ventricular impulse $(V_2)_x$ to induce an aborting atrial impulse $(A_3)_y$ arriving at the junction of the first and second pathways near the atria at a time: (1) before the inciting ventricular impulse $(V_2)_x$ traveling toward the atria through the intially conducting first or second pathway arrives at the junction of the first and second pathways near the atria; and (2) while the conducting cells of the first or second pathway other than the initially conducting first or second pathway still are refractory to excitation and therefore unable to conduct the aborting atrial impulse $(A_3)_y$ toward the ventricles through that pathway, thereby resulting in: (1) block of the aborting atrial impulse $(A_3)_y$ in the first or second pathway other than the initially conducting first or second pathway; and (2) collision in the initially conducting first or second pathway of the aborting atrial $(A_3)_y$ impulse traveling toward the ventricles and the inciting ventricular impulse $(V_2)_x$ traveling toward the atria, resulting in the aborting of the initiation of the dual pathway tachycardia which might have occurred as a result of the inciting ventricular impulse $(V_2)_x$; and wherein there is a period of time following the sensed inciting ventricular impulse $(V_2)_x$ before which an electrical stimulus delivered to the atrial cardiac cells will not result in an aborting atrial impulse $(A_3)_y$ because either: (1) the atrial cardiac cells still are refractory to excitation (not yet reconditioned) following the last received atrial impulse $A_1$ and therefore the electrical stimulus will not result in an atrial impulse; or (2) the resulting atrial impulse penetrates and blocks in the atrial side of both the first and second pathways due to the arrival of the atrial impulse at the atrial side of the first and second pathways at a time while the conducting cells of both the first and second pathways still are refractory to excitation following the last received atrial impulse $A_1$, but the conduction time of the inciting ventricular impulse $(V_2)_x$ traveling towards the atria through the initially conducting first or second pathway is sufficiently long to allow the cells of both the first and second pathways to recover excitability (become reconditioned) following the penetration of the first and second pathways by the atrial impulse induced by the electrical stimulus, then the inciting ventricular impulse $(V_2)_x$ can be conducted towards the atria through the initially conducting first or second pathway and enter the first or second pathway other than the initially conducting first or second pathway and be conducted through the first or second pathway other than the initially conducting first or second pathway toward the ventricles initiating the dual pathway tachycardia; the start time of the $(A_3)_y$ aborting zone being a time before which an electrical stimulus delivered to the atrial cardiac cells will not induce an aborting atrial stimulus $(A_3)_y$ and the stop time of the $(A_3)_y$ aborting zone being a time following the sensed inciting ventricular impulse $(V_2)_x$, after which an electrical stimulus delivered to the atrial cardiac muscle will not result in an aborting atrial impulse $(A_3)_y$ because the resulting atrial impulse will either: (1) arrive at the atrial side of the first and second pathways at a time after the inciting ventricular impulse $(V_2)_x$ traveling towards the atria through the initially conducting first or second pathway has entered the pathway other than the initially conducting first or second pathway and is being conducted through the pathway other than the initially conducting first or second pathway toward the ventricles; or (2) arrive at the atrial side of the first and second pathways after the conducting cells of the first or second pathway other than the initially conducting first or second pathway have become reconditioned to accept and conduct the atrial impulse induced by electrical stimulus towards the ventricles.

43. The system of claim 1 wherein the dual pathway tachycardia is defined further as being due to any one of atrioventricular nodal reentry or atrioventricular reentry using an anomalous atrioventricular connection for retrograde conduction, induced by an inciting ventricular impulse $(V_2)_x$ originating in the ventricles wherein the heart includes a first pathway adapted for conducting an electrical impulse generally between the atria and the ventricles and a second pathway for conducting an electrical impulse generally between the atria and the ventricles; and wherein the step of determining the echo zone is defined further as determining the $(V_2)_x$ echo zone within which an inciting ventricular impulse $(V_2)_x$ may occur resulting in dual pathway tachycardia; and wherein the step of determining the aborting zone is defined further as determining the $(V_3)_z$ aborting zone within which an aborting ventricular impulse $(V_3)_z$ may be induced in the ventricles for aborting dual pathway tachycardia which otherwise would have occurred as a result of the inciting ventricular impulse $(V_2)_x$; and wherein the step of sensing cardiac impulses is defined further as sensing ventricular cardiac impulses $V_1$'s in a heart; and wherein the step of inducing an aborting cardiac impulse is defined further as inducing an aborting ventricular impulse $(V_3)_z$ at a time within the $(V_3)_z$ aborting zone in response to sensing an inciting ventricular impulse $(V_3)_z$, the aborting ventricular impulse $(V_3)_z$ which is conducted to the ventricular side of the first and second pathways at such a time: (1) before the inciting ventricular impulse $(V_2)_x$ returning toward the ventricles through the first or second pathway other than the initially conducting first or second pathway arrives at the junction of the first and second pathways near the ventricles; and (2) while the conducting cells of the initially conducting first or second pathways still are refractory to excitation following the received inciting ventricular impulse $(V_2)_x$ and are unable to conduct the aborting ventricular impulse $(V_3)_z$ toward the atria through that initially conducting first or second pathway, thereby resulting in: (1) block of the aborting ventricular impulse $(V_3)_z$ in the initially conducting first or second pathway; and (2) collision in the first or second pathway other than the initially conducting first or second pathway of the aborting ventricular impulse $(V_3)_z$ traveling toward the atria and the inciting ventricular impulse $(V_2)_x$ traveling back toward the ventricles with the result being the aborting of the initiation of the dual pathway tachycardia by the inciting ventricular impulse $(V_2)_x$.

44. The system of claim 43 wherein the $(V_3)_z$ aborting zone is defined further as having a start time and a stop time, the start time of the $(V_3)_z$ aborting zone being a time at the end of a period of time following the sensed ventricular impulse $(V_2)_x$ before which an electrical stimulus delivered to the ventricular cardiac muscle will not result in an aborting ventricular impulse $(V_3)_z$ because either: (1) the ventricular cardiac muscle cells still are refractory to excitation [not yet reconditioned following the received inciting ventricular impulse $(V_2)_x$], *and thus the electrical stimulus will not result in a ventricular impulse*; or (2) the resulting ventricular impulse penetrates and blocks in the ventricular side of both of the first and the second pathways due to the arrival of the ventricular impulse at the junction of the first and the second pathways near the ventricles at a time while the conducting cells of both the first and the second pathways still are refractory to excitation following the received inciting ventricular impulse $(V_2)_x$ and the conduction time of the inciting ventricular impulse $(V_2)_x$ returning back towards the ventricles through the first or second pathway other than the initially conducting first or second pathway is sufficiently long in time to allow the conducting cells of both the first and second pathways to recover excitability (become reconditioned) following the penetration of the first and the second pathways by the ventricular impulse induced by the electrical stimulus, the inciting ventricular impulse $(V_2)_x$ then can be conducted towards the ventricles through the first or second pathway other than the initially conducting first or second pathway and reenter the initially conducting first or second pathway and be conducted back toward the atria through the initially conducting first or second pathway initiating the dual pathway tachycardia; and wherein the stop time of the $(V_3)_z$ aborting zone is defined further as being a time following the sensed inciting ventricular impulse $(V_2)_x$ after which an electrical stimulus delivered to the ventricular cardiac muscle cells will not result in an aborting ventricular impulse $(V_3)_z$ because the resulting ventricular impulse will either: (1) arrive at the junction of the first and the second pathways near the ventricular at a time when the inciting ventricle impulse $(V_2)_x$ traveling back toward the ventricles through the first or second pathway other than the initially conducting first or second pathway has reentered the initially conducting first or second pathway and is being conducted through the initially conducting first or second pathway back toward the atria; or (2) arrive at the junction of the first or second pathways near the ventricles at a time after the conducting cells of the initially conducting first or second pathway have become reconditioned to accept and conduct the ventricular impulse induced by the electrical stimulus towards the atria, the result being the failure to abort the dual pathway tachycardia.

45. The system of claim 1 wherein the heart includes a first pathway adapted for conducting electrical impulses between the atria and the ventricles and a second pathway adapted for conducting an electrical impulse generally between the atria and the ventricles; and wherein the step of sensing the cardiac impulses is defined further as sensing atrial impulses $A_1$'s and sensing ventricular impulses $V_1$'s in a heart; and wherein the step of inducing an aborting cardiac impulse is defined further as inducing an aborting ventricular impulse $V_3$ for aborting dual pathway tachycardia; and wherein the step of determining the echo zone is defined further as determining the $A_2$ echo zone and the $V_2$ echo zone; and wherein the step of determining the aborting zone is defined further as determining the $V_3$ aborting zone; and wherein the inciting ventricular impulse signal $V_2$ is defined further as being a ventricular impulse resulting from the conduction to the ventricles through the initially conducting first or second pathway of an inciting atrial impulse $A_2$; and wherein the inciting ventricular impulse signal $V_2$ is further defined as being: (1) the first ventricular impulse signal occuring after a sensed inciting atrial impulse $A_2$ (an atrial impulse occurring with the $A_2$ echo zone); and (2) occuring within the $V_2$ echo zone; and wherein the $V_2$ echo zone is further defined as having a start time and a stop time, the start time of the $V_2$ echo zone being defined as a time of occurrence of the first ventricular impulse after the sensed inciting atrial impulse initially conducting first or second pathway of the aborting ventricle impulse $V_3$ traveling toward the atria and the inciting atrial impulse traveling back toward the ventricles, thereby resulting in the aborting of the initiation of the dual pathway tachycardia which otherwise might have occurred as a result of the inciting atrial impulse $A_2$.

46. The system of claim 45 wherein the $V_3$ aborting zone is defined further as having a start time and a stop time, the start time of the $V_3$ aborting zone being a time after a period of time following the sensed inciting ventricular impulse $V_2$ before which an electrical stimulus delivered to the ventricular cardiac cells will not result in an aborting ventricular impulse $V_3$ because either: (1) the ventricular cardiac cells still are refractory to excitation (not yet reconditioned) following the received inciting ventricular impulse $V_2$ and thus the electrical stimulus will not result in a ventricular impulse; or (2) the resulting ventricular impulse penetrates and blocks in the ventricular side of the first and the second pathways due to the arrival of the induced ventricular impulse at the junction of the first and the second pathways near the ventricles at a time while the conducting cells of both the first and the second pathways still are refractory to excitation, and the conduction time of the inciting atrial impulse $A_2$ returning back towards the ventricles through the initially conducting first or second pathway is sufficiently long to allow the conducting cells in both the first and second pathways to recover excitability (become reconditioned) following the penetration of those pathways by the ventricular impulse induced by the electrical stimulus so the inciting atrial impulse $A_2$ can be conducted towards the ventricles through the initially conducting first or second pathway and reenter the first or second pathway other than the initially conducting first or second pathway and be conducted through the first or second pathway other than the initially conducting first or second pathway back towards the atria initiating dual pathway tachycardia; and wherein the stop time of the $V_3$ aborting zone is defined further as being a time following the sensed inciting ventricular impulse $V_2$ after which an induced electrical stimulus delivered to the ventricular cardiac cells will not result in an aborting ventricular impulse $V_3$ because the resulting ventricular impulse will either: (1) arrive at the junction of the first and the second pathways near the ventricles at a time after the inciting atrial impulse $A_2$ returning toward the ventricles through the initially conducting first or second pathway has reentered the first or second pathway other than the initially conducting first or second pathway and is being conducted through the first or second pathway other than the initially conducting first or second pathway toward the atria; or (2) arrive at the junction of the first and second pathways near the ventricles at a time after the conducting cells of the first or second pathway other than the initially conducting first or second pathway have become reconditioned to accept and conduct the induced ventricular impulse toward the atria, thereby resulting in failure to abort dual pathway tachycardia.

47. The system of claim 1 wherein the step of sensing cardiac impulses is defined further as sensing atrial impulses $A_1$'s and sensing ventricular impulses $V_1$'s and wherein the heart includes a first pathway for conducting an electrical impulse generally between the atria and the ventricles and a second pathway for conducting an electrical impulse generally between the atria and the ventricles; and wherein the step of inducing an aborting cardiac impulse is defined further to include the step of delivering an electrical stimulus $S_{(V_3)R}$ timed from a sensed inciting atrial impulse $A_2$ which would induce an aborting ventricular impulse $(V_3)_R$ which is conducted to the junction of the first and the second pathways near the ventricles at a time: (1) before the inciting atrial impulse $A_2$ traveling toward the ventricles through the initially conducting first or second pathway arrives at the junction of the first and the second pathways near the ventricles; and (2) while the conducting cells of the first or the second pathway other than the initially conducting first or second pathway still are refractory to excitation and thus cannot conduct the aborting ventricle impulse $(V_3)_R$ toward the atria through the first or second pathway other than the initially conducting first or second pathway, thereby resulting in: (1) block of the aborting ventricle impulse $(V_3)_R$ in the first or second pathway other than the initially conducting first or second pathway; and (2) collision in the initially conducting first or second pathway of the aborting ventricle impulse $(V_3)_R$ traveling toward the atria and the inciting atrial impulse $A_2$ traveling toward the ventricles, thereby resulting in the aborting of the initiation of dual pathway tachycardia by the inciting atrial impulse $A_2$; and wherein the step of determining the echo zone is defined further as determining the $A_2$ echo zone within which an inciting atrial impulse signal $A_2$ may occur resulting in dual pathway tachycardia; and wherein the step of determining the aborting zone is defined further as determining the $(V_3)_R$ aborting zone within which an aborting ventricular impulse $(V_3)_R$ may be induced in the ventricles for aborting the dual pathway tachycardia which otherwise might have occurred as a result of the inciting atrial impulse $A_2$.

48. The system of claim 47 wherein the $(V_3)_R$ aborting zone is defined further as having a start time and a stop time, the start time of the $(V_3)_R$ aborting zone occurring at a time following a period of time before which an electrical impulse delivered to the ventricular cardiac cells will not result in an aborting ventricular impulse $(V_3)_R$ because either: (1) the ventricular cardiac cells still are refractory to excitation (not yet reconditioned) following the last received ventricular impulse $V_1$ and thus the electrical stimulus will not result in a ventricular impulse or; (2) the resulting ventricular impulse penetrates and blocks in the ventricular side of both the first and second pathways due to the arrival of the ventricular impulse at the junction of the first and second pathways near the ventricles at a time while the conducting cells of the first and second pathways still are refractory to excitation following the last sensed ventricular impulse $V_1$ and the conduction time of the inciting atrial impulse $A_2$ traveling toward the ventricles through the initially conducting first or second pathway is sufficiently long to allow the conducting cells in the first and the second pathways to recover excitability (become reconditioned) following the penetration of the first and the second pathways by the ventricular impulse induced by the electrical stimulus so the inciting atrial impulse $A_2$ can be conducted towards the ventricles through the initially conducting first or second pathway and enter the first or second pathway other than the initially conducting first or second pathway and be conducted through the first or second pathway other than the initially conducting first or second pathway toward the atria initiating dual pathway tachycardia; and wherein the stop time of the $(V_3)_R$ aborting zone is defined as a time following the sensed inciting atrial impulse $A_2$ after which an electrical stimulus delivered to the ventricular cardiac cells will not result in an aborting ventricular impulse $(V_3)_R$ because the resulting ventricular impulse will either: (1) arrive at the junction of the first and second pathways near the ventricles at a time after the inciting atrial impulse $A_2$ traveling toward the ventricles through the initially conducting first or second pathway has already entered the first or second pathway other than the initially conducting first or second pathway and is being conducted through the first or second pathway other than the initially conducting first or second pathway back toward the atria; or (2) arrive at the junction of the first and second pathways near the ventricles at a time after the conducting cells in the first or second pathway other than the initially conducting first or second pathway have become reconditioned to accept and conduct the ventricular impulse induced by the electrical stimulus toward the atria, the result being in the failure to abort dual pathway tachycardia.

49. The system of claim 1 wherein the heart includes a first pathway adapted for conducting an electrical impulse generally between the atria and the ventricles and a second pathway adapted for conducting an electrical impulse generally between the atria and the ventricles; and wherein the step of sensing cardiac impulses is defined further as sensing atrial impulses $A_1$'s in a heart; and wherein the system is defined further to include the steps of:
  continuously determining the atrial cycle length (the time between maximum amplitudes of adjacent atrial impulses $A_1$'s);
  continuously determining an average atrial cycle length for a predetermined period or a predetermined number of sensed atrial impulses $A_1$'s prior to the last sensed atrial impulse $A_1$;
  determining the lapse of time between each sensed atrial impulse $A_1$ and the last sensed atrial impulse $A_1$;
  determining, for each received atrial impulse $A_1$, one of an $A_2$ echo zone, an $(A_2)_x$ echo zone and a combined $A_2$-$(A_2)_x$ echo zone or combinations thereof and determining one of an $A_3$ aborting zone, an $(A_3)_x$ aborting zone or a combined $A_3$-$(A_3)_x$ aborting zone or combinations thereof corresponding to the last determined atrial cycle length; and
  comparing the determined lapse of time between each sensed atrial impulse $A_1$ and the last sensed atrial impulse $A_1$ with one of the $A_2$ echo zone, the $(A_2)_x$ echo zone or the combined $A_2$-$(A_2)_x$ echo zone or combinations thereof determined from the last determined atrial cycle length to determine if the received atrial impulse $A_1$ occurred at a time within such determined one of the $A_2$ echo zone, the $(A_2)_x$ echo zone or the combined $A_2$-$(A_2)_x$ echo zone or combinations thereof thereby determining if the sensed atrial impulse $A_1$ is one of an inciting atrial impulse $A_2$ or an inciting atrial impulse $(A_2)_x$ or combinations thereof; and
wherein the step of inducing an aborting cardiac impulse is defined further as delivering one of an aborting electrical stimulus $S_{A3}$ or an aborting electrical stimulus $S_{(A3)x}$ or an aborting electrical stimulus $S_{A3}$-$S_{(A3)x}$ or combinations thereof at a time within the respective predetermined $A_3$ aborting zone, $(A_3)_x$ aborting zone or combined $A_3$-$(A_3)_x$ aborting zone established for the last determined atrial cycle length to the atrial cardiac muscle thereby inducing one of the aborting atrial impulse $A_3$, the aborting atrial impulse $(A_3)_x$ or the aborting atrial impulse $A_3$-$(A_3)_x$.

50. The system of claim 49 wherein the step of delivering the aborting electrical stimulus $S_{A3}$, the aborting electrical stimulus $S_{(A3)x}$ or the aborting electrical stimulus $S_{A3}$-$S_{(A3)x}$ or combinations thereof is defined further as delivering the aborting electrical stimulus $S_{A3}$, the aborting electrical stimulus $S_{(A3)x}$ or the aborting electrical stimulus $S_{A3}$-$S_{(A3)x}$ or combinations thereof at a time within the respective $A_3$ aborting zone, $(A_3)_x$ aborting zone or the $A_3$-$(A_3)_x$ aborting zone or combinations thereof as near as possible to the start time of that respective aborting zone determined for the particular average atrial cycle length, each of the $A_3$ aborting zone, the $(A_3)_x$ aborting zone and the combined $A_3$-$(A_3)_x$ aborting zone having a start time and a stop time, the start time being a time after which an aborting electrical stimulus delivered to the atrial cardiac muscle will induce an aborting atrial impulse which will result in the aborting of the initiation of dual pathway tachycardia and the stop time being the time after which the inducing of an atrial aborting impulse will not result in the aborting of the initiation of dual pathway tachycardia.

51. The system of claim 1 wherein the heart includes a first pathway adapted for conducting an electrical impulse generally between the atria and the ventricles and a second pathway adapted for conducting an electrical impulse generally between the atria and the ventricles; and wherein the step of sensing cardiac impulses is defined further as sensing ventricular impulse signals in a heart; and wherein the system is defined further to include the steps of:

continuously determining the ventricular cycle length (the time between maximum amplitudes of adjacent ventricular impulses $V_1$'s);

determining an average ventricular cycle length for a predetermined period of time or a predetermined number of sensed ventricular impulses $V_1$'s prior to the last sensed ventricular impulse $V_1$;

determining the lapse of time between each sensed ventricular impulse $V_1$ and the last sensed ventricular impulse $V_1$;

determining, for each received ventricular impulse, the $(V_2)_x$ echo zone and the $(V_3)_z$ aborting zone corresponding to the last determined average ventricular cycle length; and comparing the determined lapse of time between each sensed ventricular impulse $V_1$ and the last sensed ventricular impulse $V_1$ with the $(V_2)_x$ echo zone determined from the last determined average ventricular cycle length to determine if the received ventricular impulse $V_1$ occurred at a time within such determined $(V_2)_x$ echo zone thereby determining if the sensed ventricular impulse $V_1$ is an inciting ventricular impulse $(V_2)_x$; and wherein the step of inducing an aborting cardiac impulse is defined further as delivering an electrical stimulus $S_{(V_3)_z}$ to the ventricular cardiac muscle at a time within the $(V_3)_z$ aborting zone for the last determined average ventricular cycle length to induce an aborting ventricular impulse $(V_3)_z$ in the ventricular cardiac muscle.

52. The system of claim 1 wherein the heart includes a first pathway adapted for conducting an electrical impulse generally between the atria and the ventricles and a second pathway adapted for conducting an electrical impulse generally between the atria and the ventricles; and wherein the step of sensing the cardiac impulses is defined further as sensing the atrial impulses $A_1$'s and sensing the ventricular impulses $V_1$'s; and wherein the system is defined further to include the step of:

continuously determining the atrial cycle length (the time between maximum amplitudes of adjacent atrial impulses $A_1$'s);

continuously determining an average atrial cycle length for a predetermined period or a predetermined number of sensed atrial impulses $A_1$'s prior to the last sensed atrial impulse $A_1$;

determining the lapse of time between each sensed atrial impulse $A_1$ and the last sensed atrial impulse $A_1$;

continuously determining the ventricular cycle length (the time between maximum amplitudes of adjacent ventricular impulses $V_1$'s);

continuously determining an average ventricular cycle length for a predetermined time period or a predetermined number of sensed ventricular impulses $V_1$'s prior to the last sensed ventricular impulse $V_1$;

determining the lapse of time between each sensed ventricular impulse $V_1$ and the last sensed ventricular impulse $V_1$;

determining, for one of each received atrial impulse $A_1$ or ventricular impulse $V_1$ or combinations thereof, one of the $A_2$ echo zone, the $(V_2)_x$ echo zone, the $V_2$ echo zone or the $(A_2)_x$ echo zone and one of the $A_3$ aborting zone, the $(A_3)_x$ aborting zone, the $(A_3)_y$ aborting zone, the $(V_3)_z$ aborting zone, the $V_3$ aborting zone or the $(V_3)_R$ aborting zone or combinations thereof corresponding to the respective last determined average atrial cycle length or average ventricular cycle length or both.

53. The system of claim 52 defined further to include the step of:

comparing the determined lapse of time between each sensed atrial impulse $A_1$ and the last sensed atrial impulse $A_1$ with only a single intervening ventricular impulse $V_1$ with the $A_2$ echo zone determined from the last determined average atrial cycle length to determine if the sensed atrial impulse $A_1$ occurred at a time within such determined $A_2$ echo zone thereby determining if the sensed atrial impulse $A_1$ is an inciting atrial impulse $A_2$; and wherein the step of inducing the aborting cardiac impulse is defined further as delivering an aborting electrical stimulus $S_{A3}$ to the atrial cardiac muscle at a time within the $A_3$ aborting zone determined from the last determined average atrial cycle length.

54. The system of claim 52 defined further to include the step of comparing the lapse of time between each sensed ventricular impulse $A_1$ and the last sensed ventricular impulse $V_1$ without an intervening atrial impulse $A_1$ with the $(V_2)_x$ echo zone thereby determining if the sensed ventricular impulse $V_1$ is an inciting ventricular impulse $(V_2)_x$.

55. The system of claim 52 defined further to include the step of:

comparing the determined lapse of time between each sensed atrial impulse $A_1$ and the last sensed atrial impulse $A_1$ with only a single intervening ventricular impulse $V_1$ with the $A_2$ echo zone determined from the last determined average atrial cycle length to determine if the sensed atrial impulse $A_1$ occurred at a time within such determined $A_2$ echo zone thereby determining if the sensed atrial impulse $A_1$ is an inciting atrial impulse $A_2$; and wherein the step of inducing an aborting cardiac impulse is defined further as delivering one or a combination thereof of: (1) an aborting electrical stimulus $S_{A3}$ to the atrial cardiac cells timed from the inciting atrial impulse $A_2$ and during the $A_3$ echo zone determined for the last determined average atrial cycle length; (2) delivering an aborting electrical stimulus $S_{V3}$ to the ventricular cardiac cells timed from the inciting ventricular impulse $V_2$ and during the $V_3$ aborting zone for the last determined average atrial cycle length; and (3) delivering an aborting electrical stimulus $S_{(V_3)R}$ to the ventricular cardiac cells timed from the inciting atrial impulse $A_2$ and during the $(V_3)_R$ aborting zone for the last determined average atrial cycle length.

56. The system of claim 52 defined further to include the step of:

comparing the lapse of time between each sensed ventricular impulse $V_1$ and the last sensed ventricular impulse $V_1$ without an intervening atrial impulse $A_1$ with the $(V_2)_x$ echo zone determined from the last determined average ventricular cycle length to determine if the received ventricular impulse $V_1$ occurred at a time within such determined $(V_2)_x$ echo zone thereby determining if the received ventricular impulse signal is an inciting ventricular impulse $(V_2)_x$; and wherein the step of inducing the aborting cardiac impulse is defined further as delivering one or a combination of: (1) an aborting electrical stimulus $S_{(A_3)x}$ to the atrial cardiac cells timed from the inciting atrial impulse $(A_2)_x$ and during the $(A_3)_x$ aborting zone for the last average atrial cycle length; (2) deliver an aborting electrical stimulus $S_{(A_3)y}$ to the atrial cardiac cells timed from the inciting ventricular impulse $(V_2)_x$ and during the $(A_3)_y$ aborting zone for the last average atrial cycle length; and (3) delivering an aborting electrical stimulus $S_{(V_3)z}$ to the ventricular cardiac cell timed from the inciting ventricular impulse $(V_2)_x$ and during the $(V_3)_z$ aborting zone for the last determined average atrial cycle length.

57. The system of claim 1 wherein the step of sensing the cardiac impulses is defined further as sensing the cardiac impulses at a position on the atrial cardiac muscle as close as possible to the atrioventricular node; and wherein the step of inducing the aborting cardiac impulse is defined further as inducing the aborting cardiac impulse at a position in the atrial cardiac muscle as close as possible to the atrioventricular node.

58. The system of claim 1 wherein the heart includes a first pathway adapted for conducting an electrical impulse generally between the atria and the ventricles and a second pathway adapted for conducting an electrical impulse generally between the atria and the ventricles; and wherein the step of sensing the cardiac impulses is defined further as sensing the cardiac impulses at a position as close as possible to one of the first and the second pathways which conducts the inciting cardiac impulse.

59. The system of claim 1 wherein the heart includes a first pathway adapted for conducting an electrical impulse generally between the atria and the ventricles and a second pathway adapted for conducting an electrical impulse generally between the atria and the ventricles; and wherein the dual pathway tachycardia is defined further as being due to atrioventricular nodal reentry; and wherein the step of sensing the cardiac impulses is defined further as sensing the ventricular cardiac impulses $V_1$'s at a position on the ventricular cardiac muscle as near as possible to the ventricular side of the atrioventricular node or HIS bundle.

60. The system of claim 1 wherein the heart includes a first pathway adapted for conducting an electrical impulse generally between the atria and the ventricles and a second pathway adapted for conducting an electrical impulse generally between the atria and the ventricles; and wherein the dual pathway tachycardia is defined further as being due to atrioventricular reentry using an accessory atrioventricular pathway (or anomalous atrioventricular connection) for retrograde conduction; and wherein the step of sensing the cardiac impulses is defined further as sensing the ventricular cardiac impulses $V_1$'s at a position on the ventricular cardiac muscle as near as possible to the ventricular side of the accessory atrioventricular pathway (anomalous atrioventricular connection).

* * * * *

UNITED STATES PATENT AND TRADEMARK OFFICE
CERTIFICATE OF CORRECTION

PATENT NO. : 4,572,192                    Page 1 of 2

DATED : February 25, 1986

INVENTOR(S) : Warren M. Jackman

It is certified that error appears in the above—identified patent and that said Letters Patent is hereby corrected as shown below:

Column 34, line 48, please place the word --determining-- after the word "include".

Column 49, line 58, after the word "impulse" and before the word "initially" please insert the following:

$A_2$ before which any inciting atrial impulse $A_2$ will not be associated with the initiation of dual pathway tachycardia and the stop time of the $V_2$ echo zone being the time of occurence of the first ventricular impulse after the sensed inciting atrial impulse $A_2$ after which the inciting atrial impulse $A_2$ will not be associated with the initiation of a dual pathway tachycardia; and wherein the system is defined further as delivering an aborting electrical stimulus $Sv_3$ in response to sensing an inciting atrial impulse $A_2$ and a corresponding inciting

UNITED STATES PATENT AND TRADEMARK OFFICE
CERTIFICATE OF CORRECTION

PATENT NO. : 4,572,192    Page 2 of 2

DATED : February 25, 1986

INVENTOR(S) : Warren M. Jackman

It is certified that error appears in the above—identified patent and that said Letters Patent is hereby corrected as shown below:

ventricular impulse $V_2$, the aborting electrical stimulus $SV_3$ being timed from the sensed inciting ventricular impulse $V_2$ and resulting in the inducing of an aborting ventricular impulse $V_3$ which is conducted to the junction of the first and the second pathways near the ventricles at a time: (1) before the inciting atrial impulse $A_2$ returning toward the ventricles through the initially conducting first or second pathway arrives at the junction of the first and the second pathways near the ventricle; and (2) while the conducting cells in the first or second pathway other than the initially conducting first or second pathways still are refractory to excitation and thus unable to conduct the aborting ventricle impulse $V_3$ toward the atria through the first or second pathway other than the initially conducting first or second pathway, thereby resulting in: (1) block of the aborting ventricle impulse $V_3$ in the first or second pathway other than the initially conducting first or second pathway; and (2) collision in the

Signed and Sealed this

Thirtieth Day of December, 1986

*Attest:*

DONALD J. QUIGG

*Attesting Officer*    *Commissioner of Patents and Trademarks*